United States Patent [19]

Davie

[11] Patent Number: 5,565,626
[45] Date of Patent: Oct. 15, 1996

[54] SIMULATION OF PYROSHOCK ENVIRONMENTS USING A TUNABLE RESONANT FIXTURE

[75] Inventor: Neil T. Davie, Cedar Crest, N.M.

[73] Assignee: The United States of America as represented by the United States Department of Energy, Washington, D.C.

[21] Appl. No.: 128,963
[22] Filed: Sep. 30, 1993
[51] Int. Cl.⁶ ................................................ G01N 29/12
[52] U.S. Cl. .................... 73/579; 73/663; 73/846
[58] Field of Search ........................... 73/579, 662, 663, 73/665, 815, 841, 846, 865.9

[56] References Cited

U.S. PATENT DOCUMENTS

| | | | |
|---|---|---|---|
| 3,513,690 | 5/1970 | Pellerin et al. | 73/579 |
| 3,726,129 | 4/1973 | Thorne | 73/579 |
| 4,012,870 | 3/1977 | Berniere et al. | 73/579 |
| 4,682,490 | 7/1987 | Adelman et al. | 73/662 |
| 5,003,811 | 4/1991 | Shannon et al. | 73/12 |
| 5,245,876 | 9/1993 | Jones | 73/579 |
| 5,284,058 | 2/1994 | Jones | 73/579 |
| 5,365,788 | 11/1994 | Hobbs | 73/665 |

OTHER PUBLICATIONS

*The Shock and Vibration Handbook,* Second Edition, McGraw–Hill Book Co., 1976, pp. 1–14.

H. Luhrs, "Pyrotechnic Shock Testing—Past and Future," *The Journal of Environmental Sciences,* Nov./Dec. 1981, pp. 17–20.

N. Davie, "Pyrotechnic Shock Stimulation Using the Controlled Response of a Resonating Bar Fixture," *Proceedings—Institute of Environmental Sciences 31st Annual Technical Meeting,* 1985, pp. 344–351.

N. Davie, "The Controlled Response of Resonating Fixtures Used to Simulate Pyroshock Environments," *The Shock and Vibration Bulletin,* Bulletin 56, Part 3, 1986, pp. 119–124.

R. Bell, "Understanding The Effects of Damping Systems on Reosnant Plates," Proceedings of the 7th IMAC, vol. 2, Feb. 1989.

R. Bell et al., "Test Component Attachment Effects on Resonant Plate Pyrotechnic Shock Simulation," *1990 Proceedings—Institute of Environmental Sciences.*

D. Raichel, *Current Methods of Simulating Pyrotechnic Shock,* Jet Propulsion Laboratory, California Institute of Technology, Jul. 29, 1991.

N. Davie et al., *Pyroshock Simulation for Satellite Components Using a Tunable Resonant Fisture—Phase 1,* Sandia Report SAND92–2135, UC–700, Oct. 92, pp. 1–66.

N. Davie et al., *Pyroshock Simulation for Satellite Components Using a Tunable Resonant Fixture,* Sandia National Laboratories, Oct. 1992.

*Primary Examiner*—Richard Chilcot
*Assistant Examiner*—Eric S. McCall
*Attorney, Agent, or Firm*—Russell D. Elliott; James H. Chafin; William R. Moser

[57] ABSTRACT

Disclosed are a method and apparatus for simulating pyrotechnic shock for the purpose of qualifying electronic components for use in weapons, satellite, and aerospace applications. According to the invention, a single resonant bar fixture has an adjustable resonant frequency in order to exhibit a desired shock response spectrum upon mechanical impact. The invention eliminates the need for availability of a large number of different fixtures, capable of exhibiting a range of shock response characteristics, in favor of a single tunable system.

28 Claims, 30 Drawing Sheets

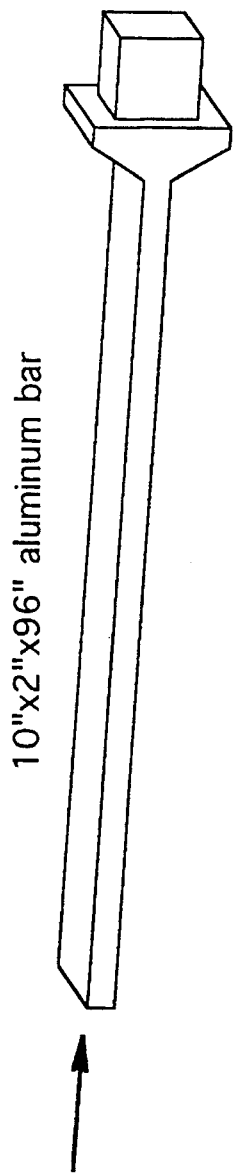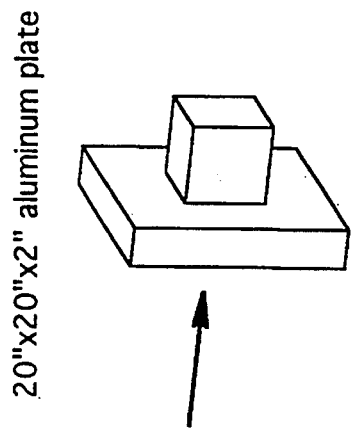
FIG. 2a
Prior Art
FIG. 2b
Prior Art

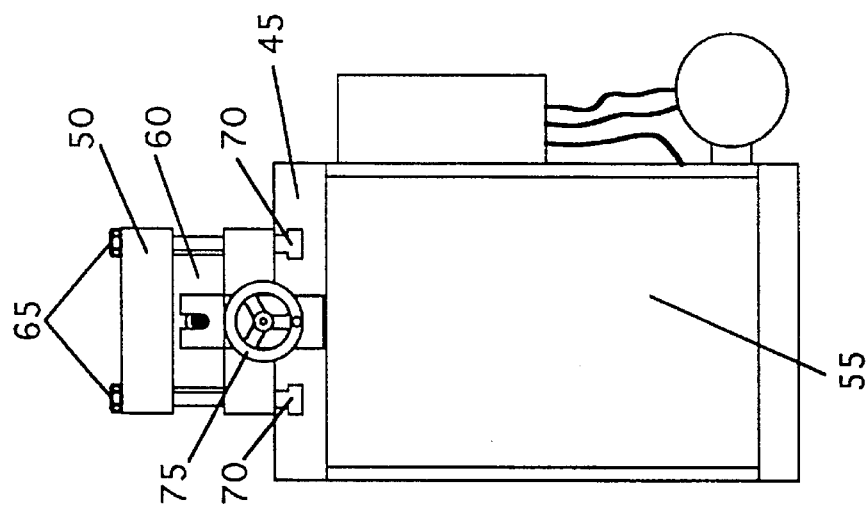
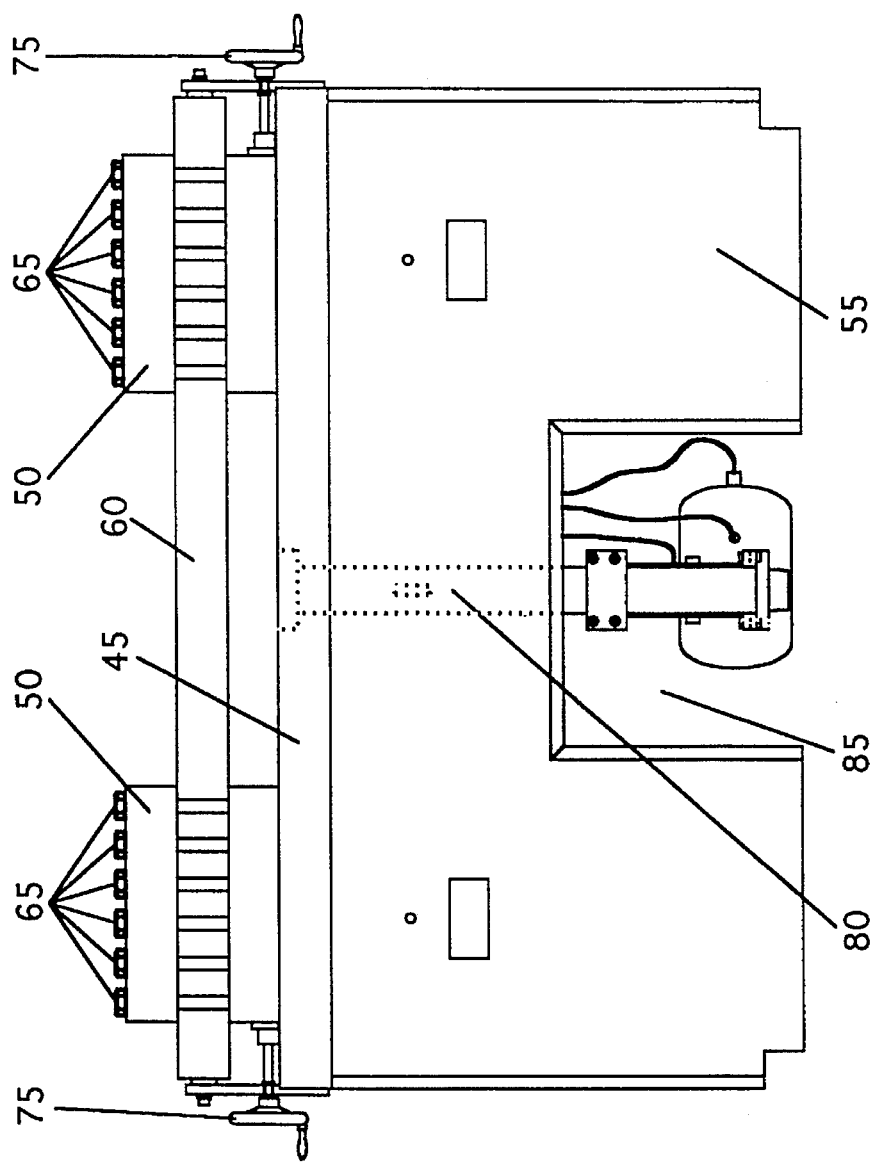
FIG. 9b
FIG. 9a

SIMULATION OF PYROSHOCK ENVIRONMENTS USING A TUNABLE RESONANT FIXTURE

GOVERNMENT RIGHTS

The United States Government has rights in this invention pursuant to Contract No. DE-AC04-76DP00789 between the U.S. Department of Energy (DOE) and AT&T Technologies, Inc. (Sandia).

BACKGROUND OF THE INVENTION

1. Field of the Invention

This invention relates generally to simulation of pyrotechnic shock for the purpose of testing electronic and other components, and more particularly, to a method and apparatus utilizing a resonant fixture capable of being tuned or conveniently reconfigured to simulate a range of different pyroshock conditions.

2. Description of the Invention

Satellite components as well as aerospace and weapon components are often subjected to pyroshock events during powered flight or deployment. As a result, system components must be qualified to this frequently severe environment. These shocks may be produced by explosive actuation devices such as detonators or linear explosives. Pyroshock-like environments can also be produced by high speed metal-to-metal impacts. The acceleration time history of a pyroshock resembles a decayed sinusoid with one or more dominant frequencies, and is characterized by high frequency, high amplitude, and a duration usually less than 20 msec. The net rigid body velocity change resulting from a pyroshock event is usually negligible. This environment is rarely damaging to structural elements, but can easily damage electronic components and assemblies.

The severity of a pyroshock environment is usually characterized using a shock response spectrum (SRS). The SRS used is normally the MAXIMAX spectrum which is the maximum absolute value acceleration response. An SRS is a plot of the maximum response of a single degree of freedom (SDOF) system as a function of the natural frequency of the SDOF. The magnitude of the SRS at a given frequency is the maximum absolute value response that would be produced on an SDOF system with the same natural frequency if it were subjected to the shock time history (base input). The SDOF damping ratio is a parameter which must be selected for the SRS calculation. This is normally chosen to be 5% for pyroshock data analysis.

The shock spectrum is viewed as a measure of damage potential. This is based on the assumption that the failure mechanism of a typical component can be modeled as a SDOF system. The application of the SRS as a design tool has historically resulted in robust component design for weapon and other components. When conducting pyroshock simulations, an SRS may be used as a means to quantifiably compare test environments with test requirements. In addition, efforts may be made to match time history peak G's, and total duration if these data are available.

Due to the high cost and complexity of most aerospace systems, component qualification using the actual pyroshock environment on complete assemblies is not reasonable. In addition, design margin cannot be determined with this approach. For these reasons, laboratory simulations of pyroshock environments are conducted on individual components and subassemblies. Traditional haversine pulse tests do not produce an adequate pyroshock simulation with regard to time history or SRS comparison. In general, the use of a haversine pulse test to simulate a pyroshock environment would result in a severe over-test at low frequencies, since the haversine test has considerably more velocity change than a pyroshock with comparable peak G's.

Presently, pyroshock environments are simulated in the aerospace industry by one of the following methods:

1. Electrodynamic Shaker.

This method can accurately produce a desired SRS within closely specified tolerances, but amplitude and frequency limitations of the equipment greatly restrict its applicability.

2. Live Ordnance with System Structure.

Since the actual system structure and live ordnance are used, this method has the potential to produce a shock virtually identical to the expected field environment. With this present technology, all the very high frequencies (>10 KHz) associated with near-field pyroshock events are produced with this method. The cost of the test structure, however, is usually prohibitive, unless large numbers of identical tests are to be conducted. The use of live ordnance may have a wide repeatability tolerance, and does not easily allow the test levels to be increased so that an adequate design margin can be assured.

3. Live Ordnance with Mock Structure.

This method has most of the same features as 2, above, except that some cost savings are attributed to the use of a mass mock-up structure. These savings may be negated by the need for some trial-and-error testing to attain the desired component input, where geometric similarity was used in 2 to attain the same result.

4. Live Ordnance with Resonant Hate Fixture. This method further reduces test cost, and is a candidate for general purpose testing, due to the use of a generic resonant plate fixture. Since live ordnance is used, all the very high frequencies associated with near-field pyroshock events are produced with this method. However, a great amount of trial-and-error testing may be required to obtain the desired component input.

5. Mechanical Impact with Mock Structure.

Mechanical impacts do not produce the very high frequencies associated with the stress pulse in the immediate vicinity of a pyrotechnic device. However, most components in aerospace systems are isolated by enough intermediary structure such that the shock at the component location is not dominated by these very high frequencies. Instead, the shock at the component is dominated by the structural response to the pyrotechnic device, and has dominant frequencies which are typically less than 10 KHz. For these components, a mechanical impact (e.g. using a projectile or pendulum hammer) can produce a good simulation of the pyroshock environment. Test amplitudes can easily be increased or decreased by simply increasing or decreasing the impact speed. Frequency content can be controlled by the use of various pads affixed at the point of impact. Simulated pyroshock environments have been produced using mechanical impacts on system structures (or similar mass mock-ups). According to this method, the structure is impacted at the same point as the actual pyrotechnic device, and test conditions are experimentally adjusted so that the response at the component is appropriate. Due to the cost of the test structure, and the large amount of trial-and-error testing required, this method is impractical in most cases.

6. Mechanical Impact with Resonant Fixture.

In this method, a resonant fixture (typically a flat plate) is used instead of a mock structure. This significantly reduces cost, and allows for general purpose testing since the fixturing is not associated with a particular structural system. The mechanical impact excites the fixture into resonance which provides the desired input to a test component mounted on the fixture. Historically, test parameters such as plate geometry, component location, impact location, and impact speed, have been determined in a trial-and-error fashion. In general, this method produces a simulated environment which has its energy concentrated in a relatively narrow frequency bandwidth. This feature may not be desirable for some pyroshock environments. It should be noted here that a suitable resonant fixture for use in this method may also be a bar impacted either at the end or at some point along the length of the bar. The use of a bar-shaped resonant fixture is discussed in detail, below.

The methods just described are more fully explained in the following references: Daniel R. Raichel, "Current Methods of Simulating Pyrotechnic Shock", Pasadena, Calif.: Jet Propulsion Laboratory, California Institute of Technology, Jul. 29, 1991; Monty Bai, and Wesley Thatcher, "High G Pyrotechnic Shock Simulation Using Metal-to-Metal Impact", *The Shock and Vibration Bulletin*, Bulletin 49, Part 1, Washington D.C.: The Shock and Vibration Information Center, September, 1979; Neil T. Davie, "The Controlled Response of Resonating Fixtures Used to Simulate Pyroshock Environments", *The Shock and Vibration Bulletin*, Bulletin 56, Part 3, Washington D.C.: The Shock and Vibration Information Center, Naval Research Laboratory, August 1986; Neil T. Davie, "Pyrotechnic Shock Simulation Using the Controlled Response of a Resonating Bar Fixture", Proceedings of the Institute of Environmental Sciences 31st Annual Technical Meeting, 1985; "The Shock and Vibration Handbook", Second Edition, page 1–14, Edited by C. M. Harris and C. E. Crede, New York: McGraw-Hill Book Co., 1976; Henry N. Luhrs, "Pyroshock Testing—Past and Future", Proceedings of the Institute of Environmental Sciences 27th Annual Technical Meeting, 1981.

Much of the trial-and-error required with Method 6, above, has been eliminated by designing the resonant fixture such that its dominant lower mode or modes correspond to the dominant frequencies in the component test requirement. Using simple design principles, the fixture can be designed based only on the test requirement, and therefore, automatically has the desired frequency content. Minimal experimental adjustment is required to attain the proper amplitude and mechanical damping.

Existing pyroshock simulation technology according to Method 6, above, requires maintaining a large inventory of test fixtures in order to accommodate differing test requirements. In the alternative, resonant fixtures may need to be designed and built to custom specifications. Even given such test-specific preparations, trial-and-error is a significant factor in achieving desired testing conditions. All of these factors are costly and may result in difficulty in controlling test input.

In a recent U.S. Patent, the use of damping masses is described as a method to affect SRS in the context of a mechanical impact pyroshock simulator. U.S. Pat. No. 5,003,811, Shannon, et at., "Shock Testing Apparatus", discloses an apparatus wherein a longitudinal bar is impacted at one end and damping masses are clamped at preselected positions along the bar. According to the Shannon, et at., disclosure, an objective of the invention is to "tune" the resonant fixture in order to affect the SRS. Although Shannon, et al., seek to achieve a smoothing of the SRS for a given resonant fixture, their invention cannot use a single tunable apparatus to simulate different resonant frequencies.

SUMMARY OF THE INVENTION

Disclosed here are a method and apparatus capable of solving the problems noted above concerning existing technology. According to the invention, a tunable resonant fixture is provided which will lead to easier control of test input, lower test cost, and a reduction in resonant fixture inventory. In addition, it will be possible to extend this method to test large test items such as satellite components.

Accordingly, it is an object of the present invention to provide a method and apparatus wherein a resonant fixture is supported by a first and second clamping means which are adjustable such that the portion of the beam which is suspended between the clamping means is capable of resonating upon impact.

It is another object of the present invention to provide a method and apparatus whereby the length of the resonating portion of the beam may be adjusted in order that the beam, when impacted, will exhibit a desired shock response spectrum.

It is yet another object of the present invention to provide a method and apparatus whereby a range of shock environments may be simulated using a single tunable fixture rather than requiring different resonant fixtures to simulate different test conditions.

Upon further study of the specification and appended claims, further objects and advantages will become apparent to those skilled in the art. These objects have been attained by providing a method and apparatus for simulating pyrotechnic shock for the purpose of qualifying electronic components for use in weapons, satellite, and aerospace applications which comprise using a single resonant bar fixture which has an adjustable resonant frequency in order to exhibit a desired shock response spectrum upon mechanical impact.

BRIEF DESCRIPTION OF THE DRAWINGS

FIGS. 2a and 2b illustrate prior art pyroshock simulation fixtures.

FIGS. 3a and 3b show graphic representations of time history and SRS for the 1000 Hz bar shown in FIG. 2a.

FIGS. 9a and 9b schematically illustrate a larger apparatus for use with the present invention.

DETAILED DESCRIPTION OF THE INVENTION

Figure 1:
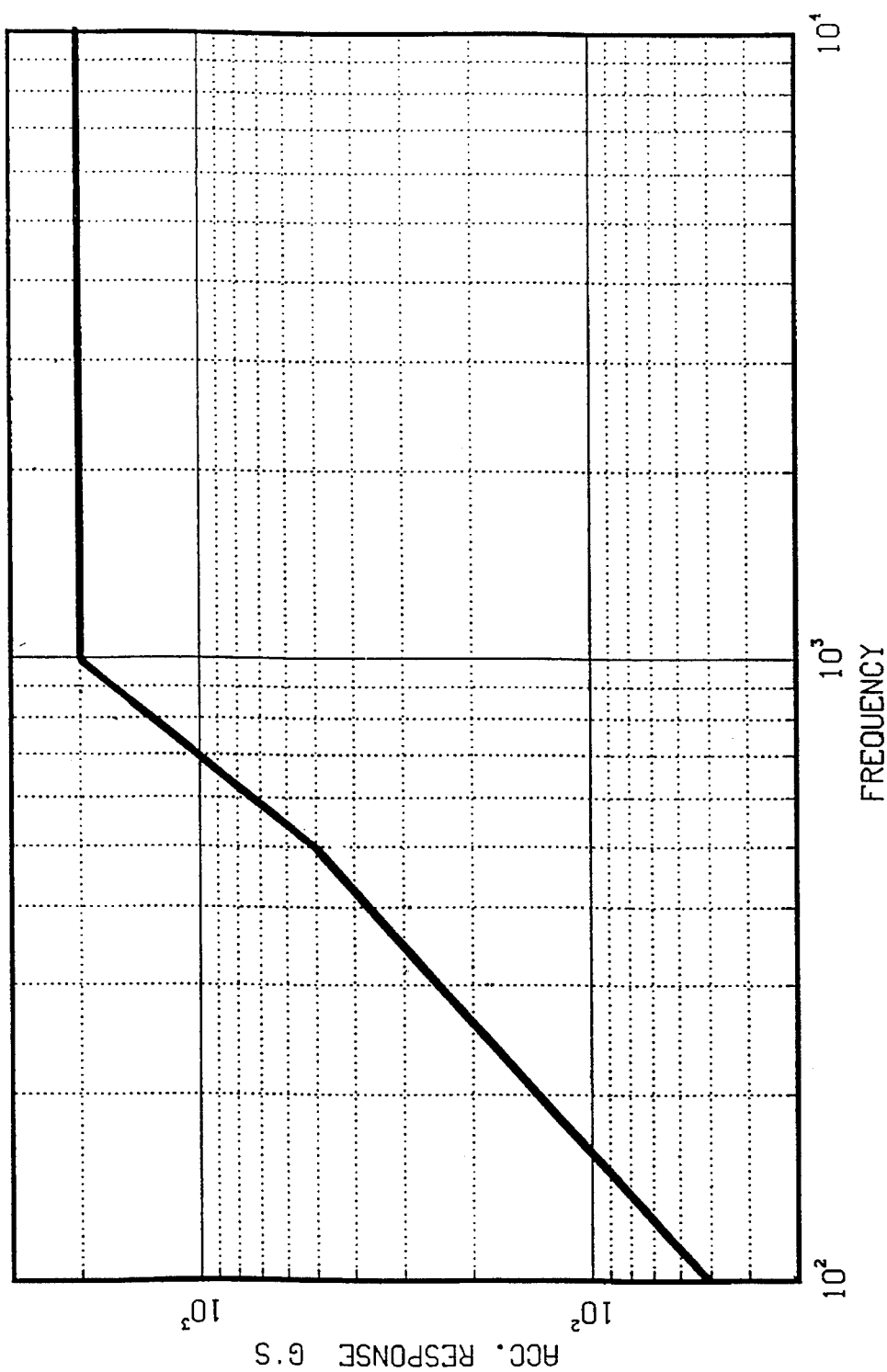
FIG. 1 shows a graphic representation of a typical shock response spectrum test specification.

FIG. 1 shows a "typical" component test requirement, as specified by an SRS wherein acceleration response in "G's" is plotted as a function of frequency. The SRS exhibits a characteristic "knee" (in this example at 1000 Hz) where the spectrum changes from a steep slope to a nearly constant amplitude. Assuming that the component to be tested is an electronic package with a 5"×5" mounting base, a resonant fixture must be designed such that its first mode of vibration has a frequency at or near the SRS knee. The fixture must also be large enough to allow the component to fit on an antinodal area of the fixture's first mode. Suitable prior art resonant fixture geometries may include either a rectangular aluminum plate which is excited into it's first bending mode, or an aluminum bar which is excited into it's first longitudinal mode. FIGS. 2a and 2b show schematic illustrations of possible test configurations and fixture dimensions that could be used for each of the two types of resonant fixtures just mentioned. FIG. 2a illustrates the Hopkinson Bar Technique and FIG. 2b illustrates the Resonant Plate Technique. For both figures, the horizontal arrow at the left shows the direction of impact, and the test item is depicted as the rectangular solid shown at the right of the figure. Examples of suitable dimensions for the resonant fixtures are shown in the figures.

Figure 3A:
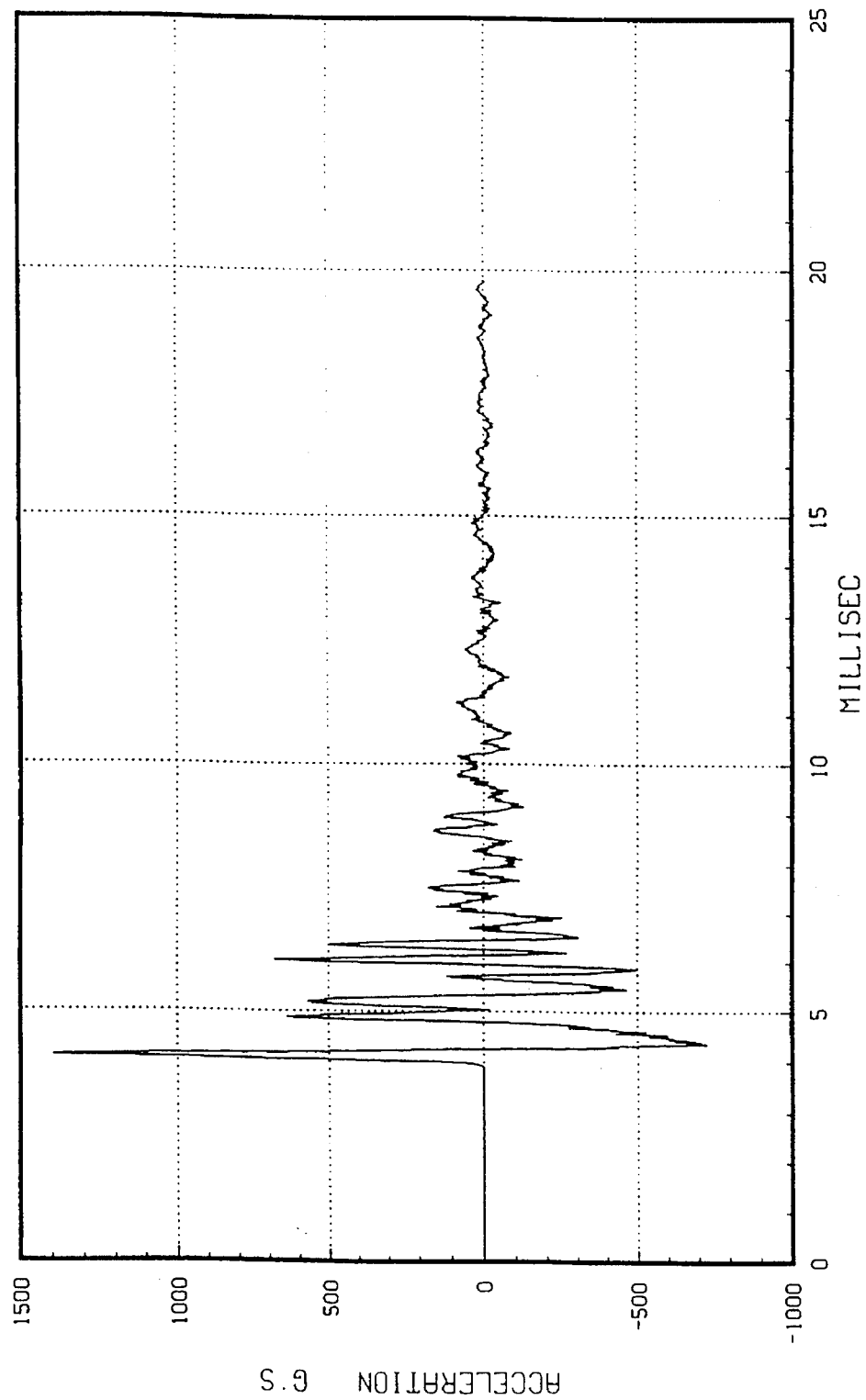
Figure 3B:
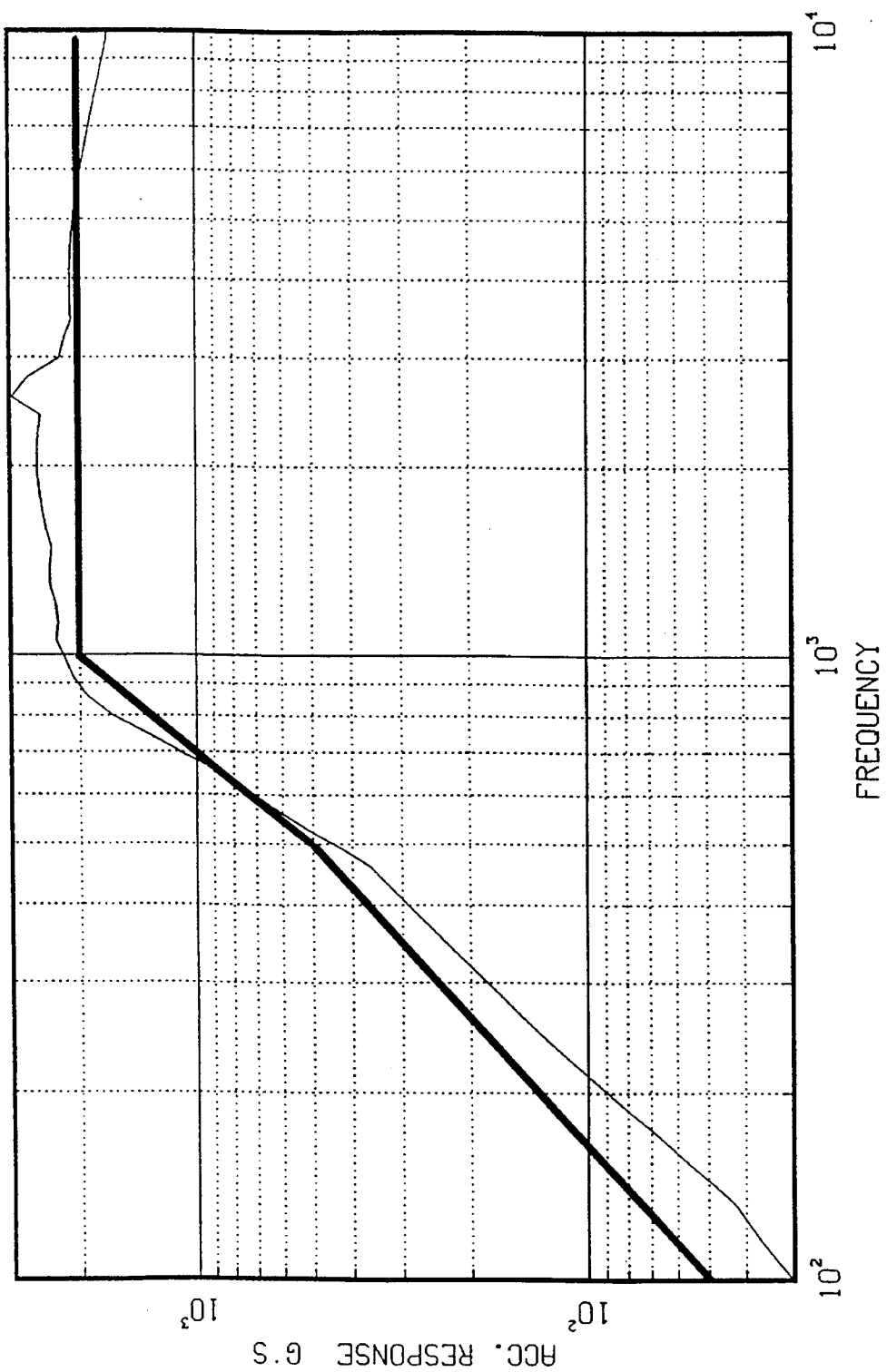

FIGS. 3a and 3b show actual SRS data obtained from a longitudinal bar fixture compared to the test requirement. In FIG. 3a, acceleration in G's is shown versus time in milliseconds. In FIG. 3b, acceleration is shown versus frequency. The bold curve represents a typical SRS test requirement which specifies test levels that must be closely matched by the pyroshock simulation equipment while the superimposed lighter curve represents actual test dam. Similar results can be expected for the bending plate fixture. It should be emphasized that the fixture geometry is determined from the test requirement without any trial-and-error testing. In particular the fixture is designed such that its first resonant frequency is approximately the same as the "knee" frequency of the test requirement. Only a minimal amount of experimental adjustment is required to determine impact speed (i.e. SRS amplitude), and fixture damping. The mechanical damping is accomplished by attaching various clamps or metal bars to the resonant fixture.

Since the plates used for the bending configuration are relatively thick, the first bending mode frequency is closely predicted by equations for beam bending frequencies. The following equation is used as a design tool for selecting the fixture geometry. ("The Shock and Vibration Handbook," ibid.)

$$f_n = K_n \frac{t}{L^2}$$ Equation 1 where:

$f_n = n^{th}$ bending frequency, (Hz)

$$K_n = \frac{A_n}{2\pi} \sqrt{\frac{E}{12\rho}}$$, for a beam of rectangular section $A_n$=a constant dependent on the $n^{th}$ mode E=modulus of elasticity, (psi)

$\rho$=density, (lb-sec$^2$/in$^4$)

t=beam thickness, (in)

L=length of beam (or long dimension of rectangular plate), (in)

For aluminum, $K_1$=203,800

Note: This equation applies to beams of various end conditions. The constants $A_n$ are the same for a free-free beam, and a fixed-fixed beam. The free-free condition applies to a bending plate fixture, and the fixed-fixed condition applies to the tunable resonant fixture.

The corresponding equation for the longitudinal modes of the bar fixture is as follows (Bai and Thatcher, "High G Pyrotechnic Shock Simulation Using Metal-to-Metal Impact," ibid.):

$$f_n = \frac{c}{2L}$$ Equation 2 where:

$f_n = n^{th}$ longitudinal frequency c=wave speed in bar ($\approx$199,000 in/sec for aluminum)

L=bar length, (in)

For a test requirement with a different knee frequency, the above equations can be used to calculate new resonant fixture dimensions in order to simulate pyroshock environments for a wide variety of test requirements. Absent the present invention, a large inventory of resonant fixtures must be maintained in order to cover the range of SRS knee frequencies encountered. This may not be an extreme burden where test requirements are for small (<8" cube) weapon components, and resonant fixtures are relatively small. Recent trends, however, have shown an increase in requests for testing of satellite and missile payload components with mounting bases up to 24"×24". Expanding fixture inventories to allow testing of these large components would be costly and space consuming. This has been a primary motivation to develop a single tunable resonant fixture to replace an entire inventory of fixtures.

Another advantage of a tunable resonant fixture is that it would allow small adjustments in the knee frequency to compensate for the effects that different-sized components would have on the response of the resonant fixture. With the present methods, a resonant fixture designed to give the correct input to a lightweight component might not provide quite the same input to a more massive component. This is because the resonant frequency of the plate would be slightly lowered. (Bell, "Understanding the Effects of Damping Systems on Resonant Plates," Proceedings of the 7th IMAC, Vol. 2, Feb. 1989, and Bell and Zimmerman, "Test Component Attachment Effects on Resonant Plate Pyrotechnic Shock Simulation," Proceedings of the Institute of Environmental Sciences Annual Technical Meeting, 1990. This difference might be enough to cause the SRS for the massive component to fall outside the test requirement tolerance bounds. In this case, a slightly thicker plate would need to be fabricated to accommodate the massive component.

The method currently in use also imparts a small rigid body velocity change to the test item. This velocity change is often greater than that of the actual pyroshock being simulated. The tunable resonant fixture concept described herein eliminates this rigid body velocity change due to the way the fixture is held. In general, the tunable resonant fixture concept will yield lower cost, more controllable pyroshock simulation.

Previous research led to the development of a tunable resonant bar fixture, for which the first, second or third mode could be selectively excited. (Davie, "Pyrotechnic Shock Simulation Using the Controlled Response of a Resonating Bar Fixture," ibid.) With this earlier method, a single fixture could be used to produce pyroshock simulations for three different SRS knee frequencies. However, a continuously adjustable resonant frequency was desired, and the tunable resonant bar does not meet this requirement.

Figure 4:
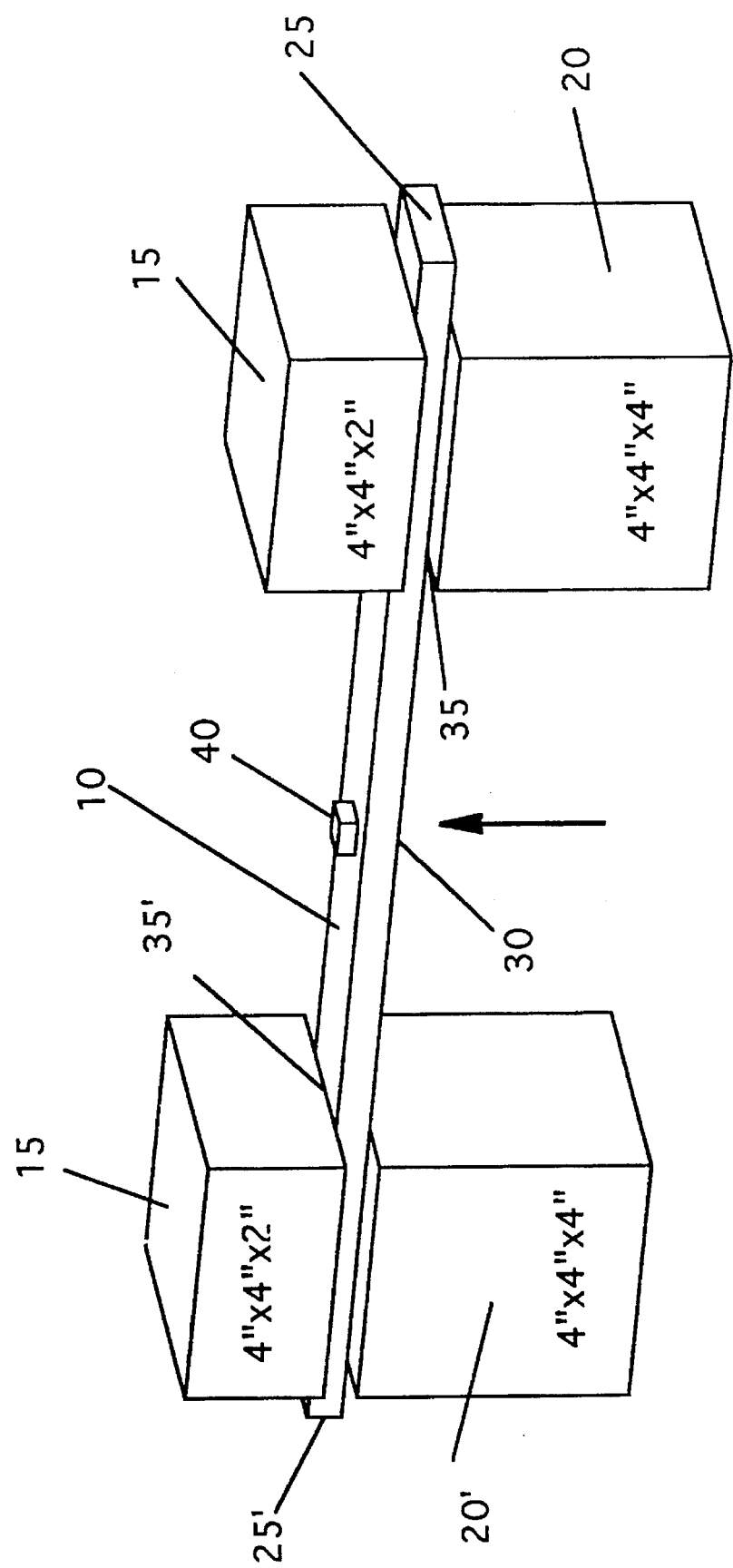
FIG. 4 schematically illustrates a small scale apparatus for practicing the present invention.

Referring to FIG. 4, in an embodiment which demonstrates the principles of the invention, the mechanical system conceived to provide a continuously adjustable resonant frequency includes a beam (10) bearing two ends (25, 25') and a center (30) wherein the beam is supported according to fixed-fixed end conditions. The beam is rigidly clamped in two positions between upper massive blocks (15, 15') and lower massive blocks (20, 20'). The clamping is performed in the regions between the center of the beam and the ends of the beam, and the precise location of the clamping can be adjusted to achieve desired test conditions. The direction of impact is shown by the vertical arrow at the center of the figure.

The first bending mode of this system can be roughly predicted for a simple beam with fixed-fixed end conditions. The frequency of the first bending mode can be adjusted by moving the clamping location of the two masses, and thus changing the length of the free span of the beam between the masses. For an ideal beam with fixed-fixed end conditions, the first bending mode is calculated from Equation 1, where L is the length of the beam between the fixed ends (35, 35'). The center (30) of the beam span is the area of maximum response (antinode) for the first bending mode. This is the optimum point of impact to excite the beam into its first mode.

In the preferred embodiment, a test component (40) mounted on the beam opposite to the impact is subjected to a maximum response at the first bending frequency. As with existing resonant fixture test methods, the impact duration must be of the appropriate duration so that the impact energy is delivered to the first mode of the fixture. If the duration is too short, higher bending modes will be excited. This could be desirable for some pyroshock environments that do not follow the characteristic SRS shown in FIG. 1. In most cases, however, the impact duration can be adjusted for first mode excitation by using various felt, or cardboard pads at the point of impact.

In order to prove the tunable resonant fixture concept described above, a small scale apparatus such as that shown in FIG. 4 was fabricated. This apparatus consisted of a 20" long ×2" wide ×½" thick resonant beam. Each end of the beam was clamped as shown between a pair of steel blocks using ⅜" bolts (not shown). The position of the clamping blocks could be adjusted in order to vary the free length of the beam between the blocks. Endevco 7270A™ accelerometer was attached to the midpoint of the resonant beam to measure the acceleration response of the beam. The opposite side of the beam was then struck with a small hammer such that the first bending mode was excited. Measurements were made for several different distances between the clamping blocks. Two of these experiments are examined in detail in the following paragraphs.

Figure 5A:
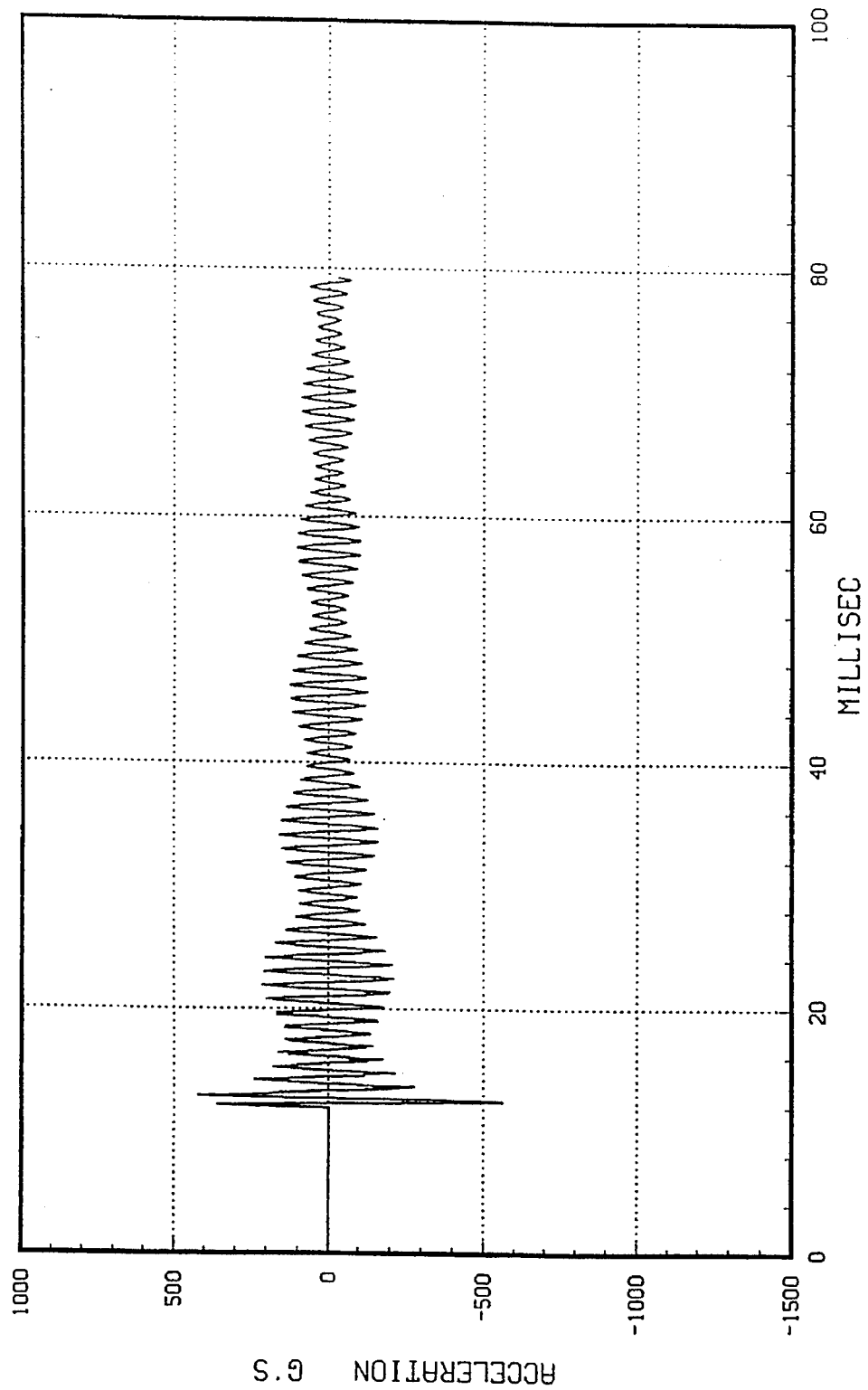
FIGS. 5a and 5b show graphic representations of time history and SRS for a small scale apparatus, with a 10" space, no pads.
Figure 5B:
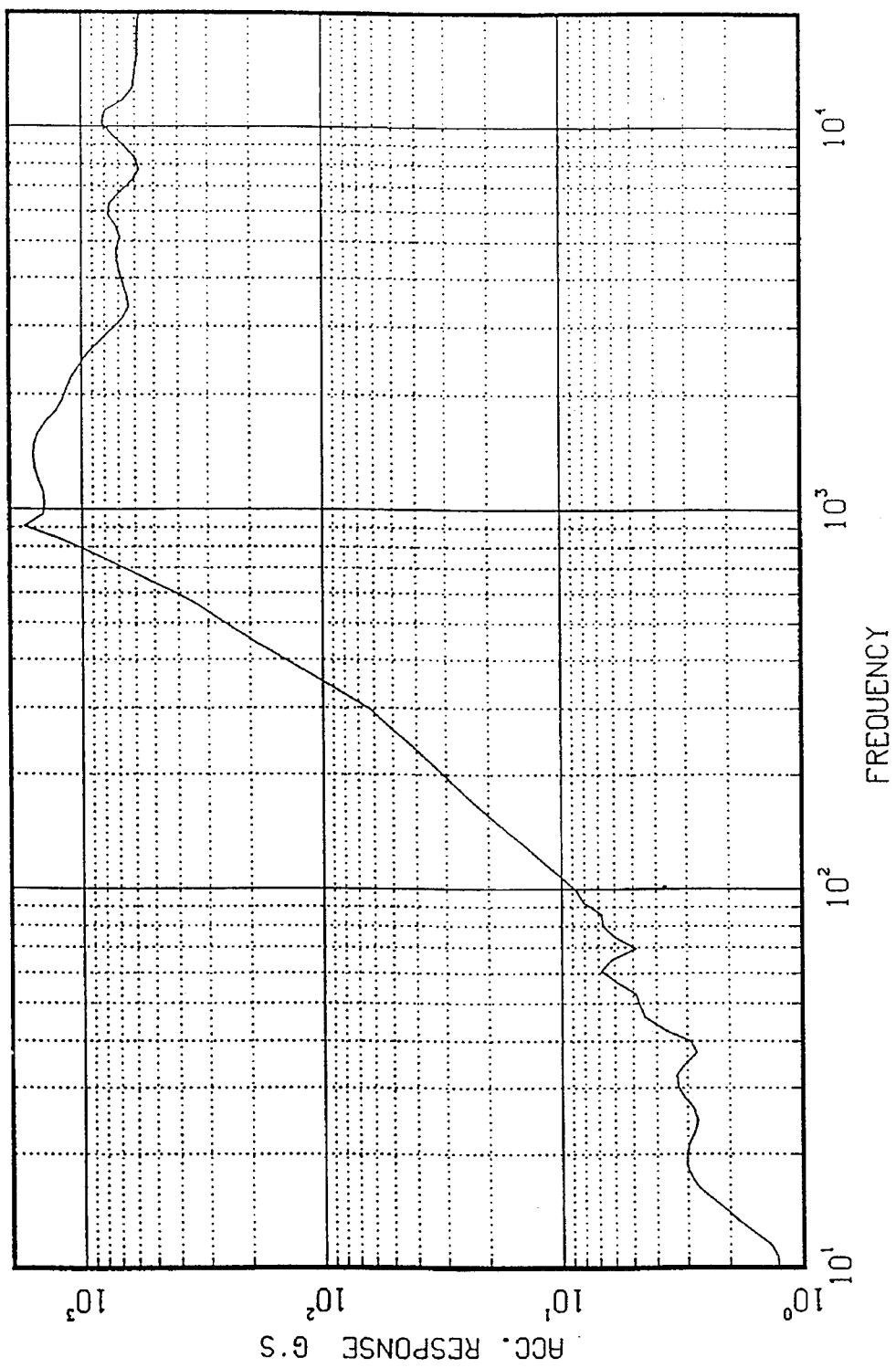

FIG. 5a shows the acceleration time history for a spacing of 10" between the blocks. FIG. 5b shows the corresponding SRS. The SRS knee occurs at about 900 Hz. calculation of the Fourier transform magnitude revealed two dominant frequencies at 810 Hz, and 900 Hz. These closely spaced modes explain the "beat" frequency envelope appearance of the dam. The first bending frequency of 1020 Hz, for a perfectly fixed-fixed beam with this geometry, was calculated from Equation 1.

Figure 6A:
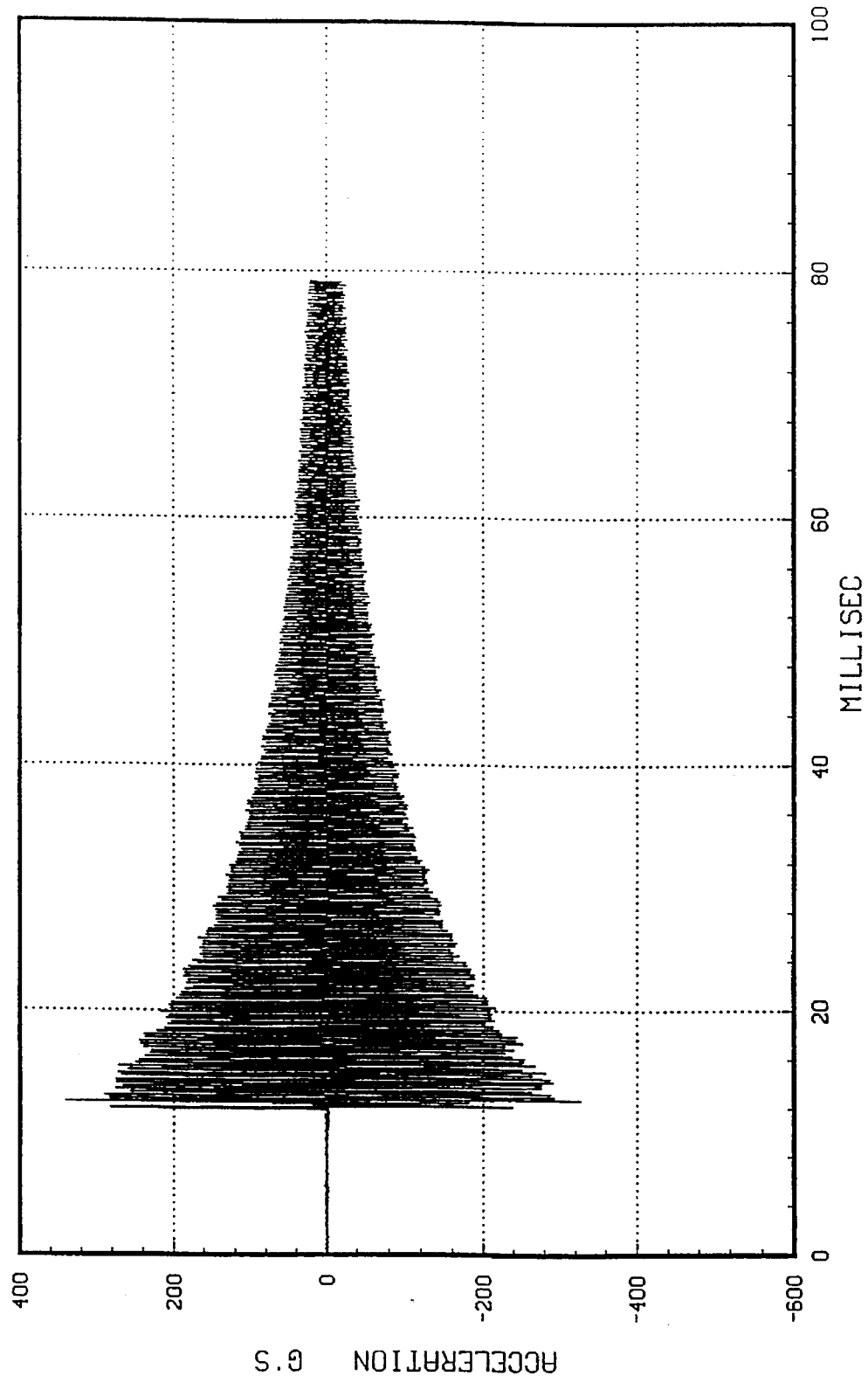
FIGS. 6a and 6b show graphic representations of time history and SRS for a small scale apparatus, with a 4" space, no pads.
Figure 6B:
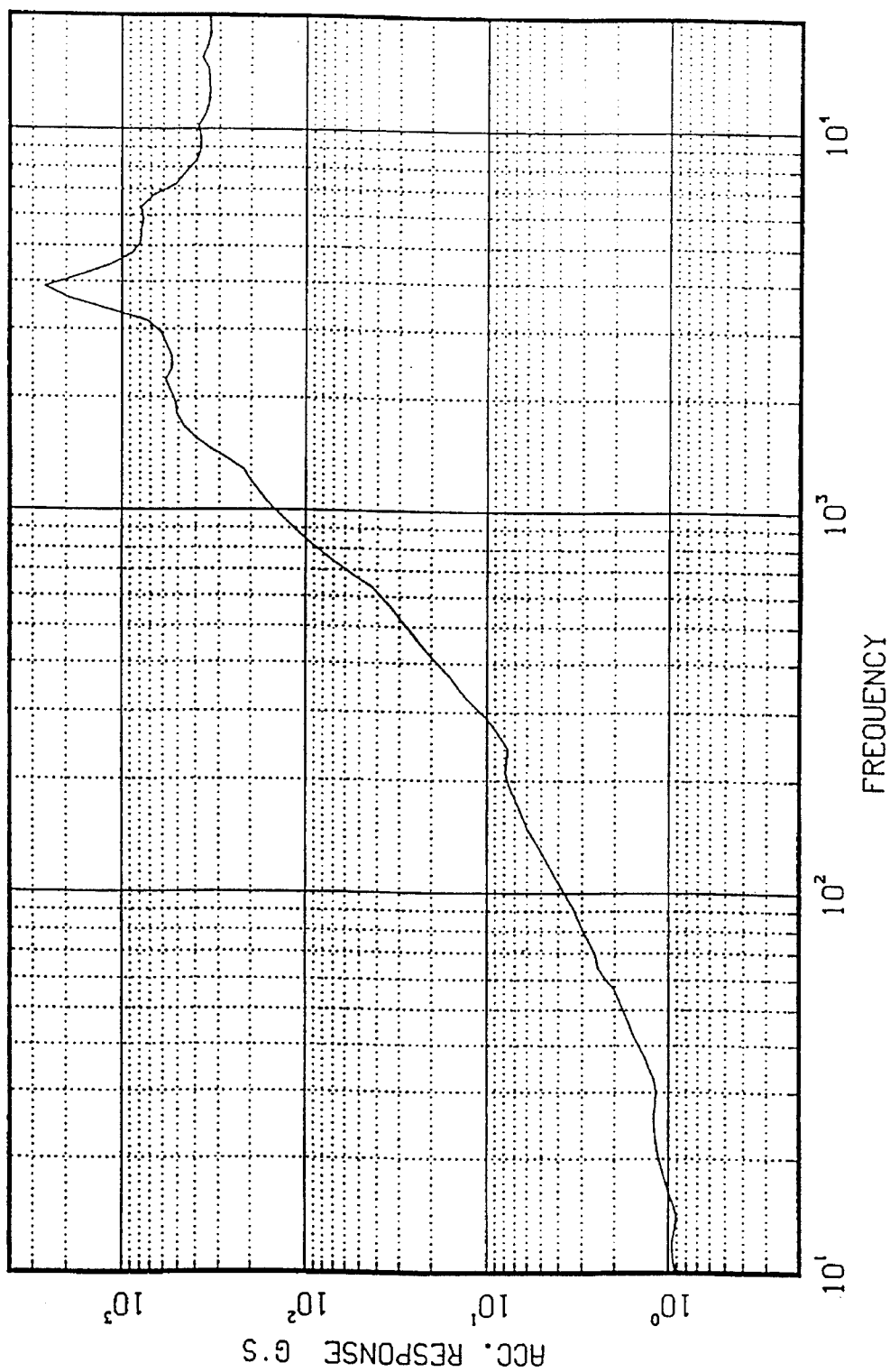

FIGS. 6a and 6b shows the acceleration time history and corresponding SRS for a spacing of 4" between the blocks. The SRS knee occurs at about 3900 Hz. A calculation of the Fourier transform magnitude revealed a dominant frequency at 3900 Hz. A comparable first bending frequency of 6350 Hz, for a perfectly fixed-fixed beam with this geometry, was calculated from Equation 1.

Several conclusions and observations can be made from these experiments. The dominant beam frequency is tunable by varying the position of the blocks. This frequency approximately corresponds to the frequency that would be calculated for a perfectly fixed-fixed beam, although, the deviation increases at higher frequencies. The shape of the SRS was desirable for pyroshock simulation, since the slope preceding the knee was about 12 dB/octave. The beam response was only lightly damped, which results in a relatively high SRS amplitude at the knee frequency. With this low damping it could be difficult to keep the total duration as short as required for the pyroshock simulation.

Following the above experiments, several methods to increase the damping were investigated. In the first method, a putty-like material known as Duxseal™ was stuck onto portions of the beam between the two sets of blocks. This resulted in a dramatic increase in the damping of the beam's response. Although this material provided the desired result, it was felt that it would be difficult to obtain repeatable results from one test set up to the next. In addition, the effectiveness of this material at a much larger scale was unknown.

Figure 7A:
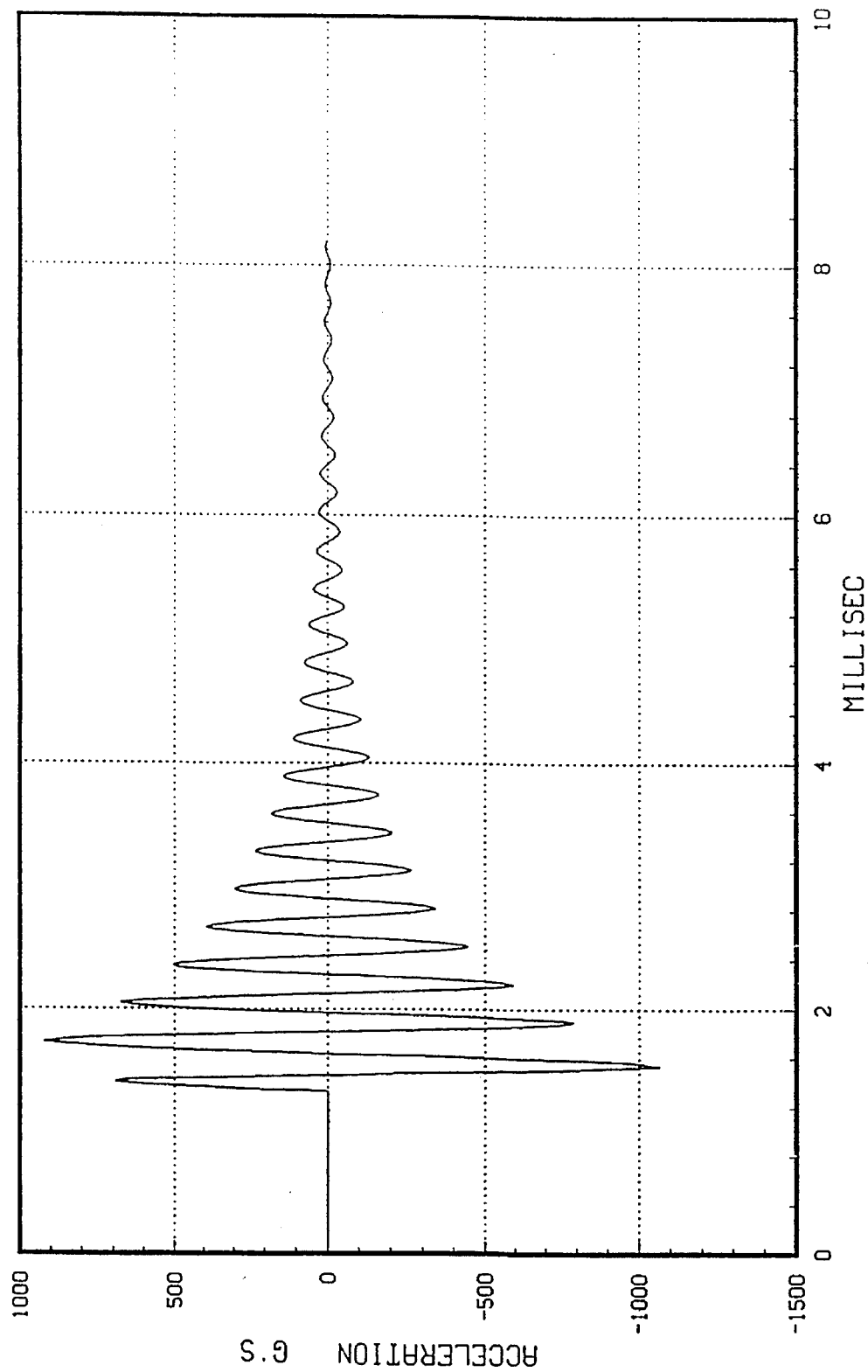
FIGS. 7a and 7b show graphic representations of time history and SRS for a small scale apparatus, with a 4" space, with pads.
Figure 7B:
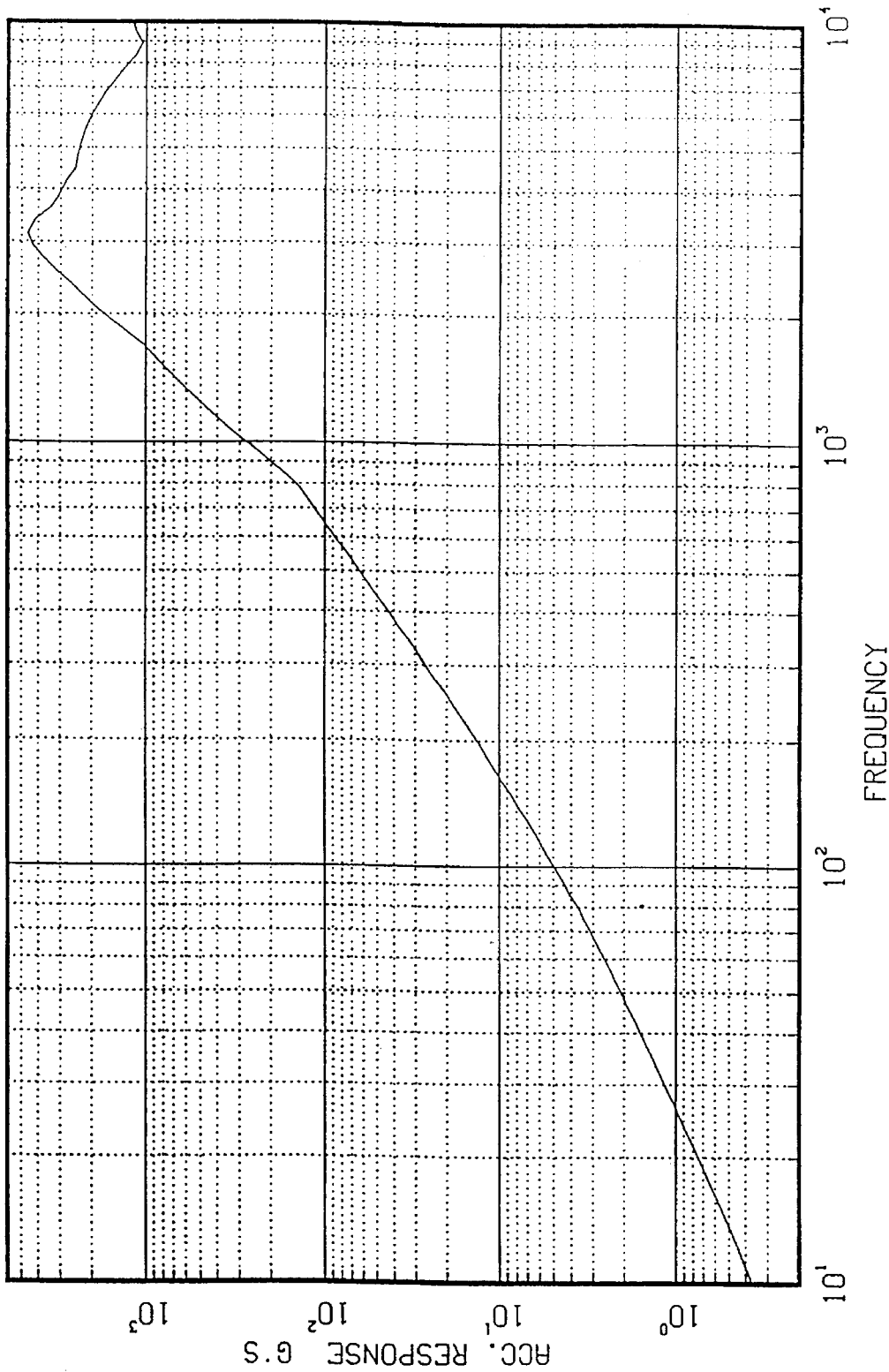

For the next method various materials (paper, plastic, cardboard, and neoprene) were inserted between the beam and the clamping blocks. From these experiments, the best material was judged to be ⅟₁₆" thick neoprene. FIGS. 7a and 7b shows the acceleration time history and corresponding SRS for a 4" spacing between the blocks, and with the neoprene pads inserted. Comparing these results with those depicted in FIGS. 6a and 6b (showing data for the same configuration without the pads) it is evident that the SRS curve is smoother for the neoprene damped configuration and has an improved shape for pyroshock simulation. Also, the resonant frequency decreased from about 3900 Hz with no pads to about 3200 Hz with the neoprene pads. This change is due to the fact that the pads reduce the clamping rigidity of the blocks.

Figure 8:
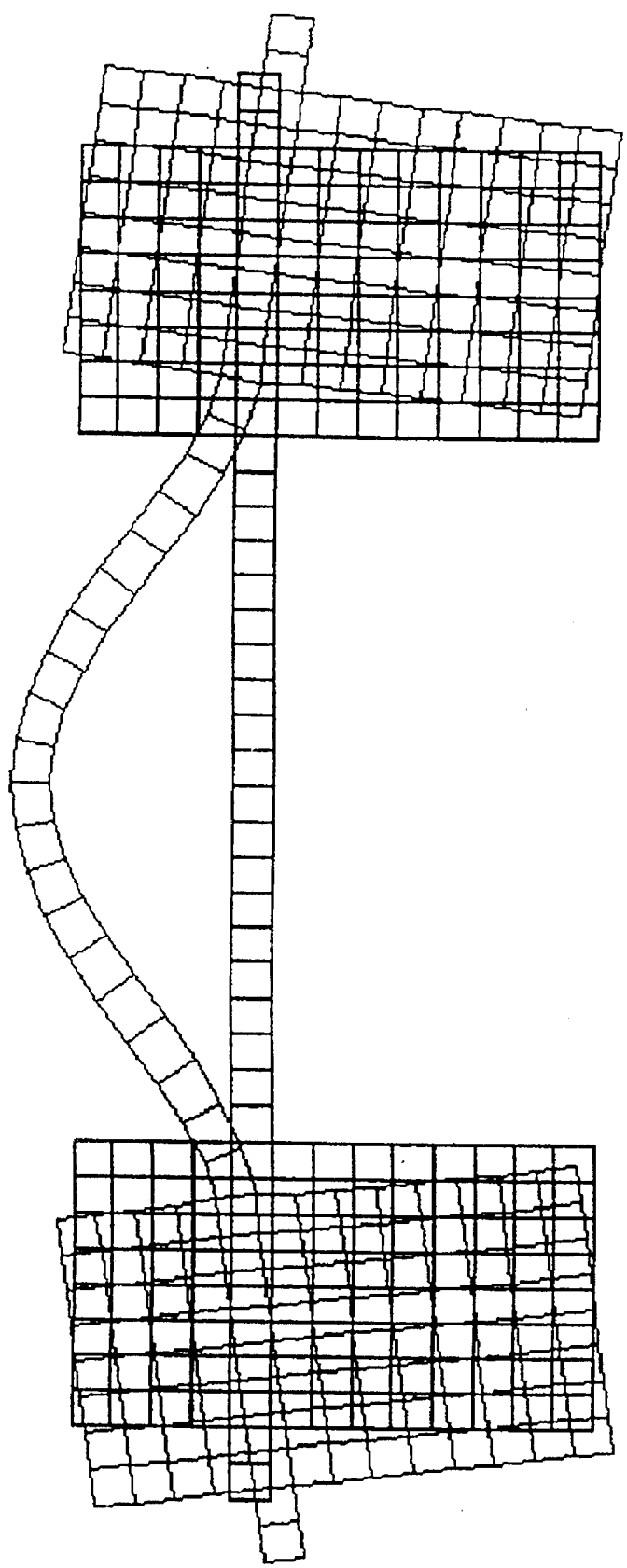
FIG. 8 shows a graphic representation of mode shape of the dominant bending mode of a small scale apparatus.
Figure 10A:
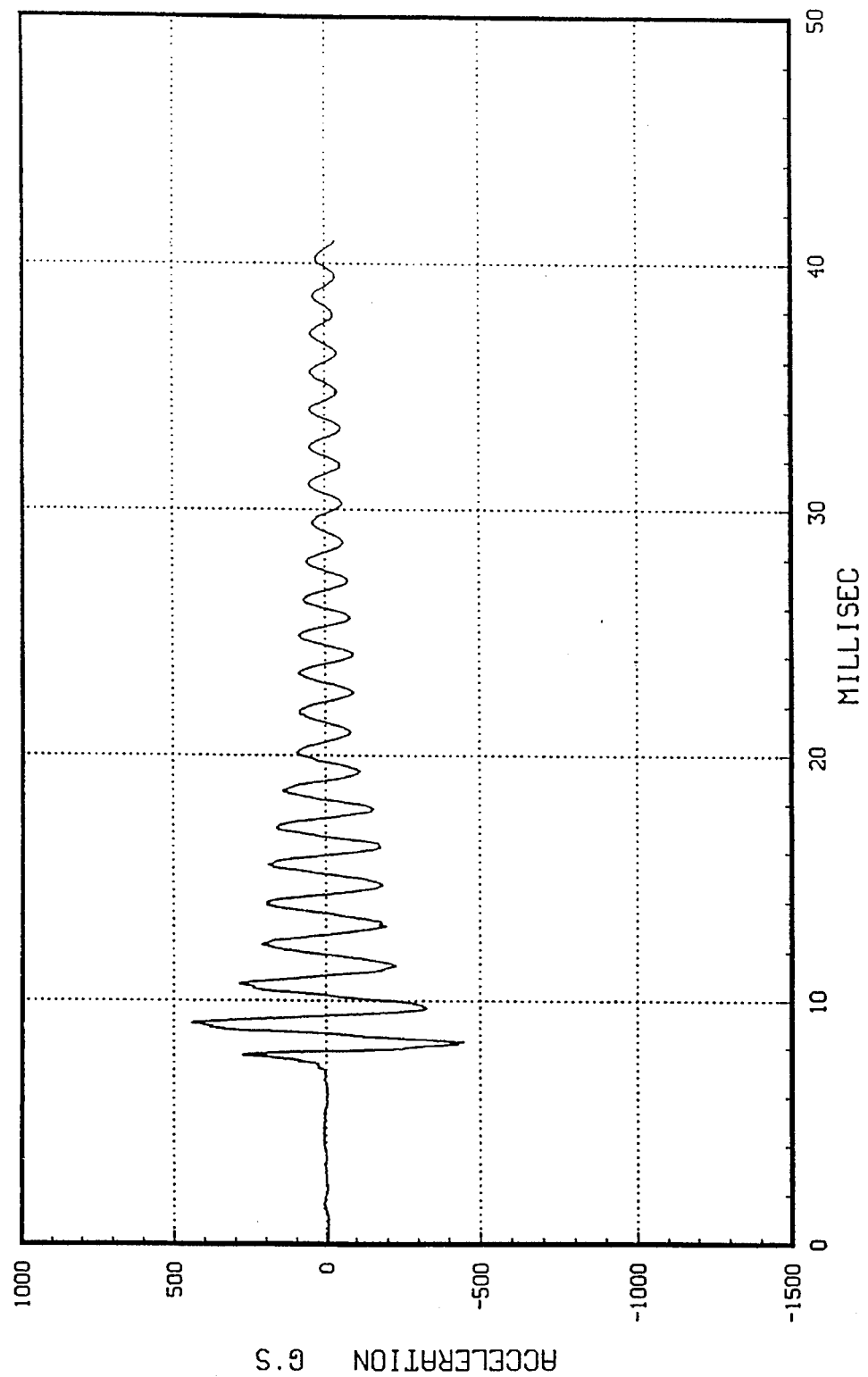
FIGS. 10a and 10b show graphic representations of time history and SRS for a larger apparatus, with a 30" space, without pads.
Figure 10B:
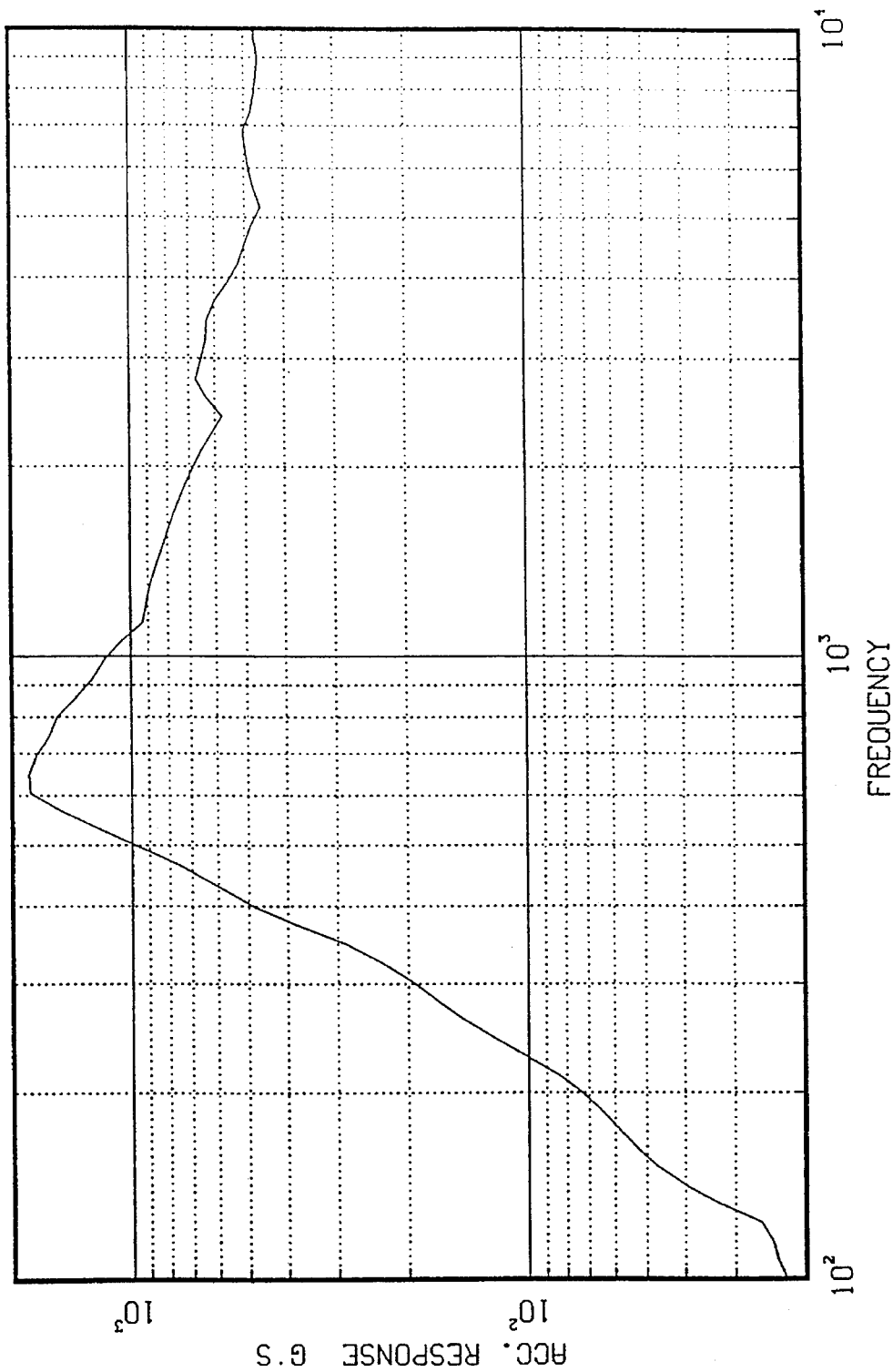
Figure 11A:
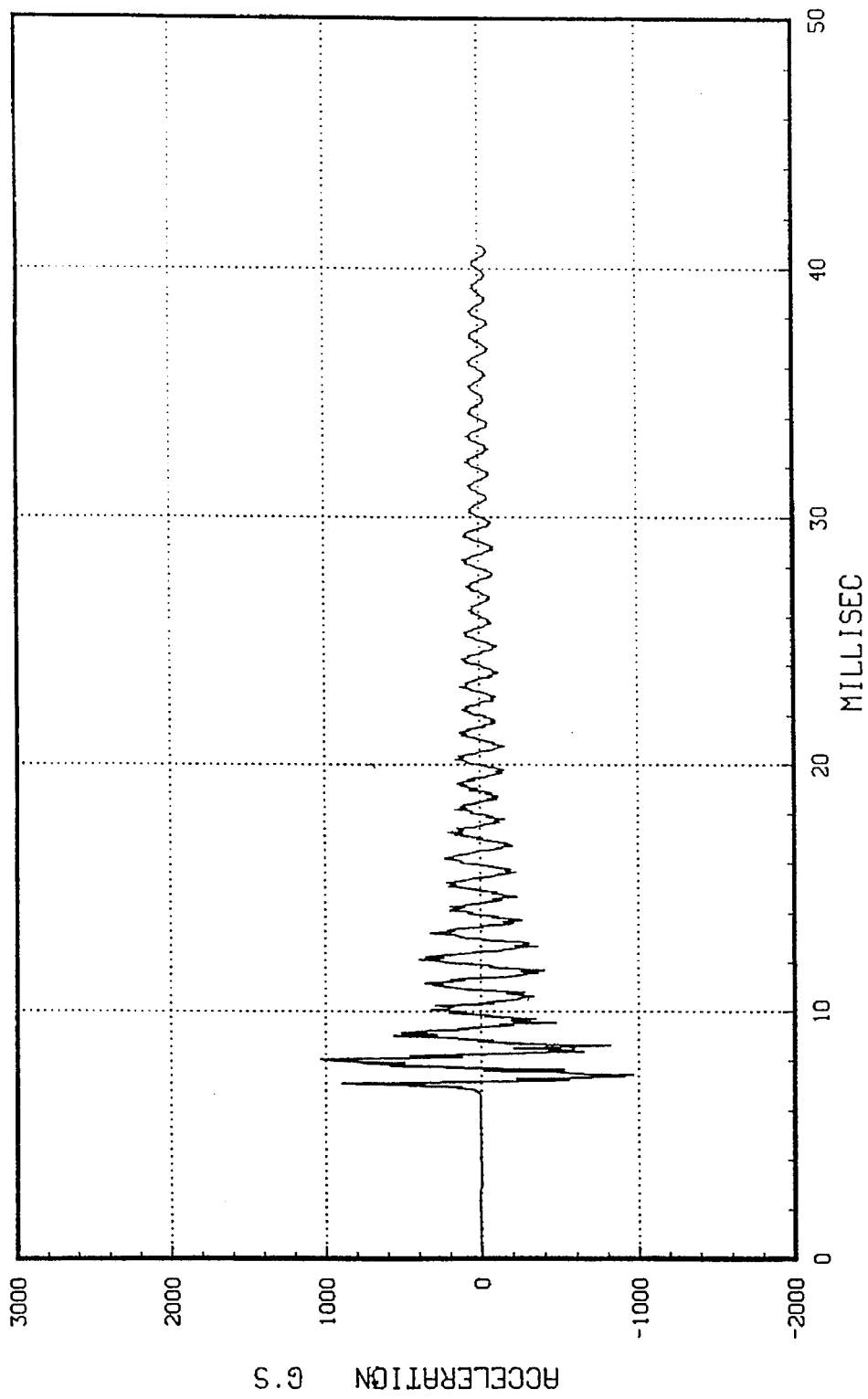
FIGS. 11a and 11b show graphic representations of time history and SRS for a larger apparatus, with a 24" space, without pads.
Figure 11B:
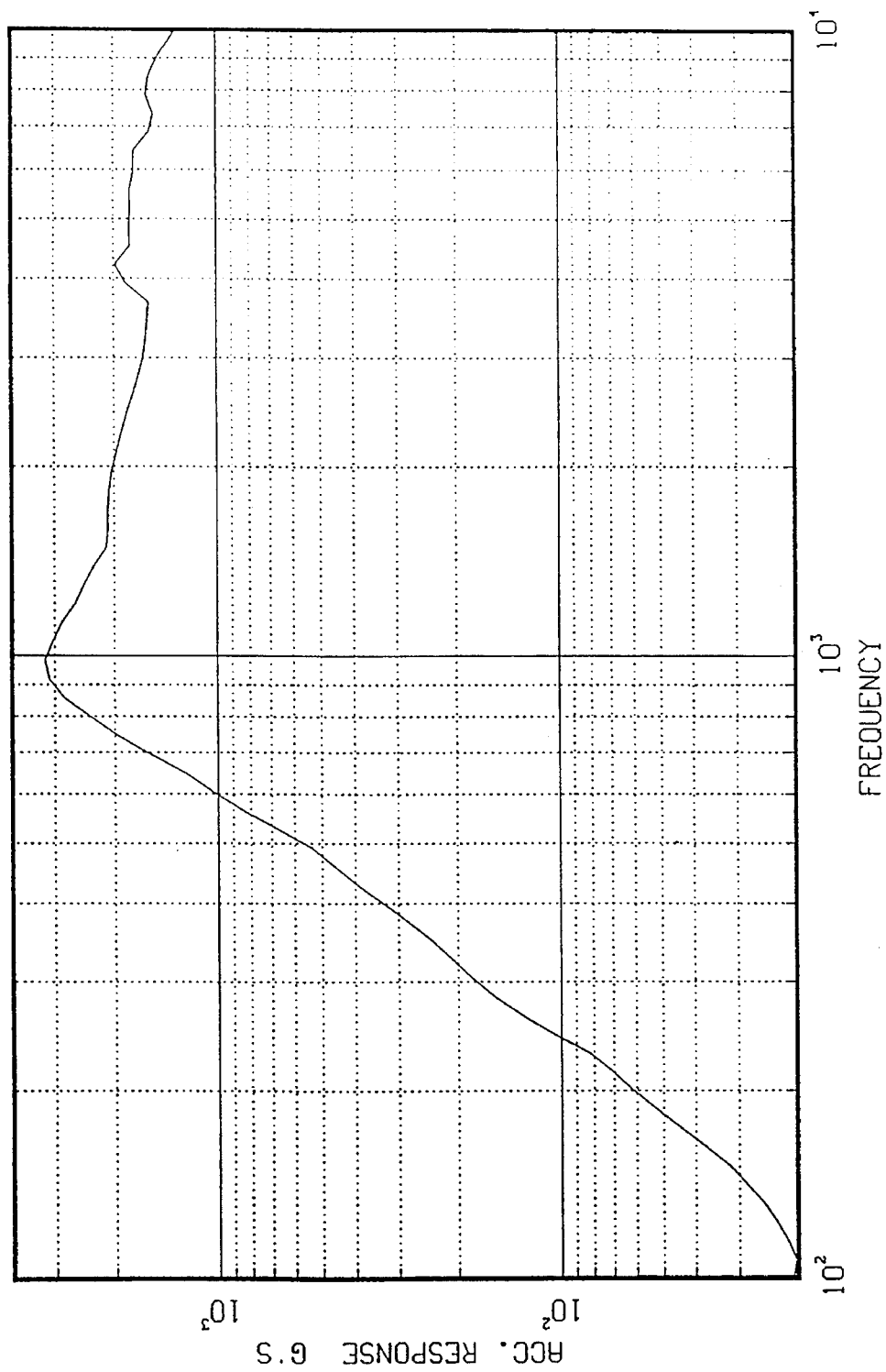
Figure 12A:
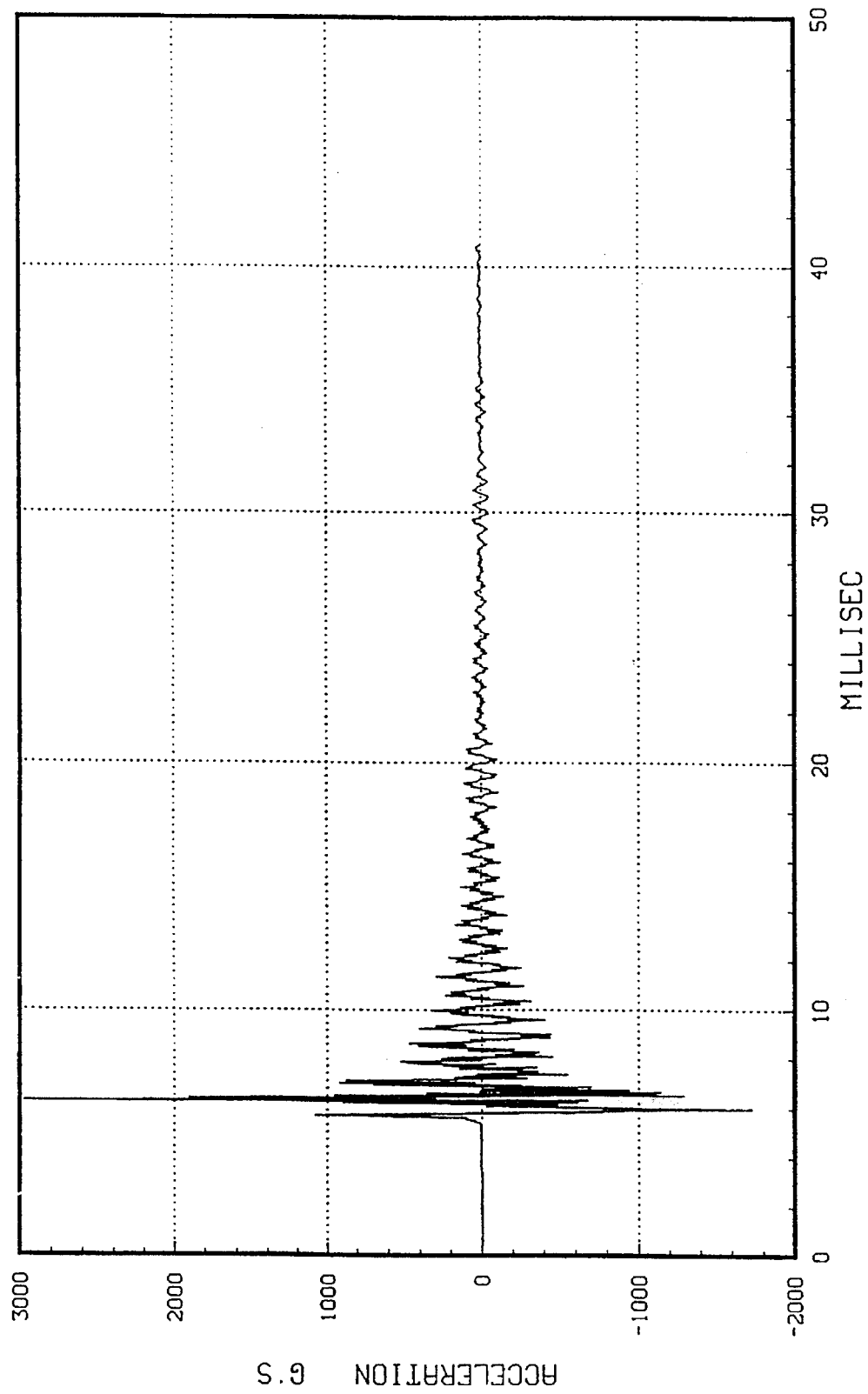
FIGS. 12a and 12b show graphic representations of time history and SRS for a larger apparatus, with a 18" space, without pads.
Figure 12B:
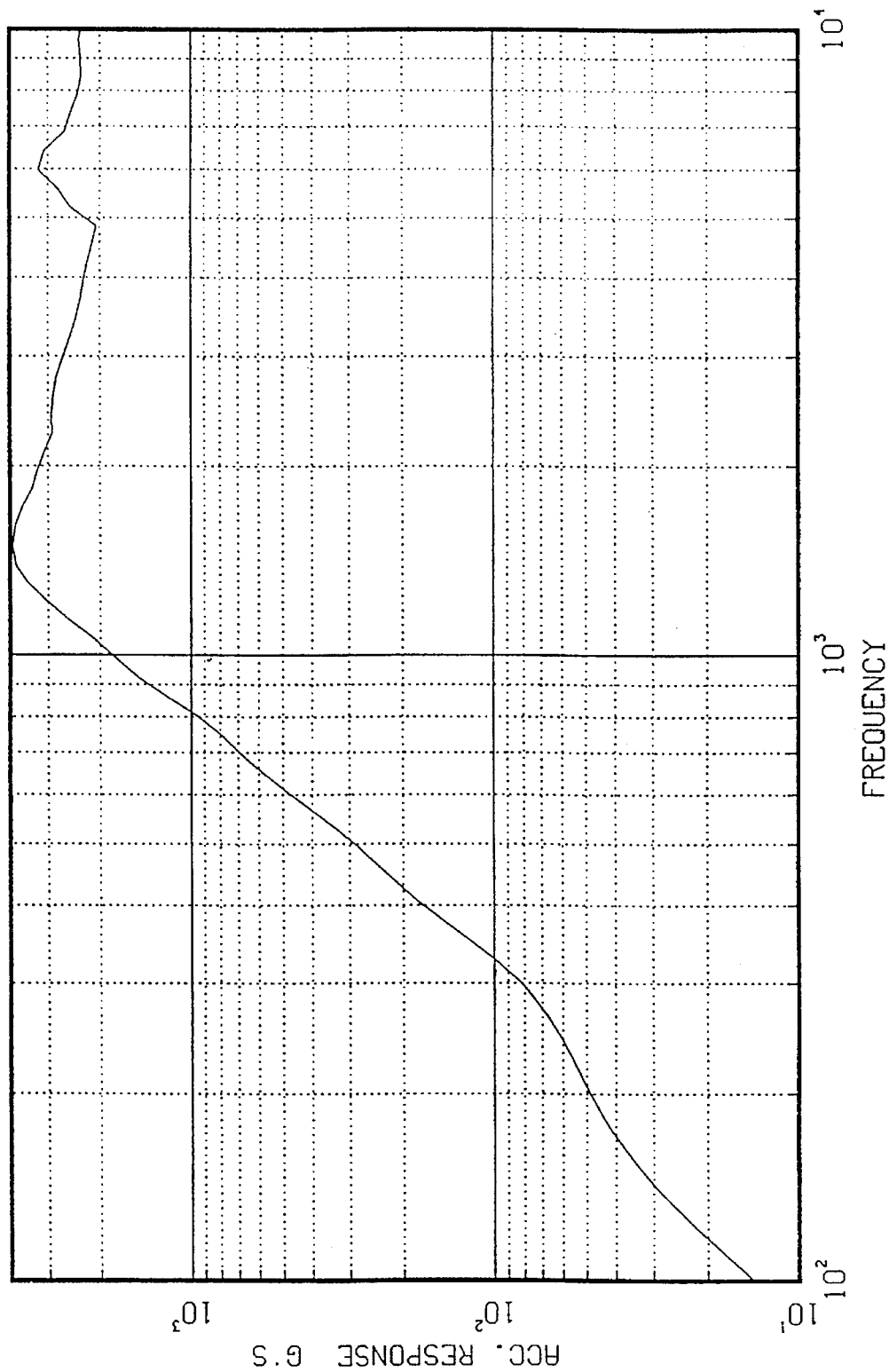
Figure 13A:
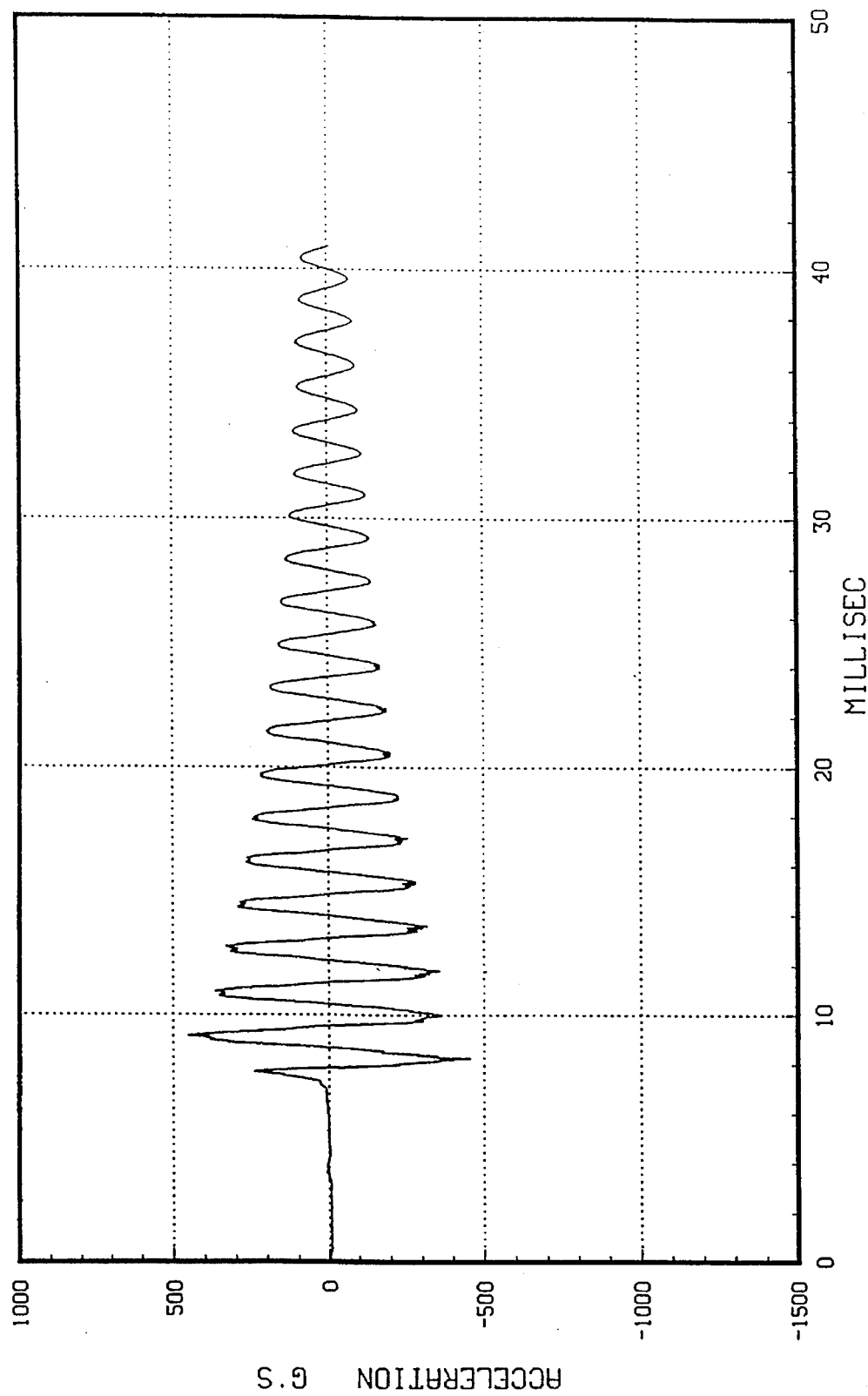
FIGS. 13a and 13b show graphic representations of time history and SRS for a larger apparatus, with a 30" space, with pads.
Figure 13B:
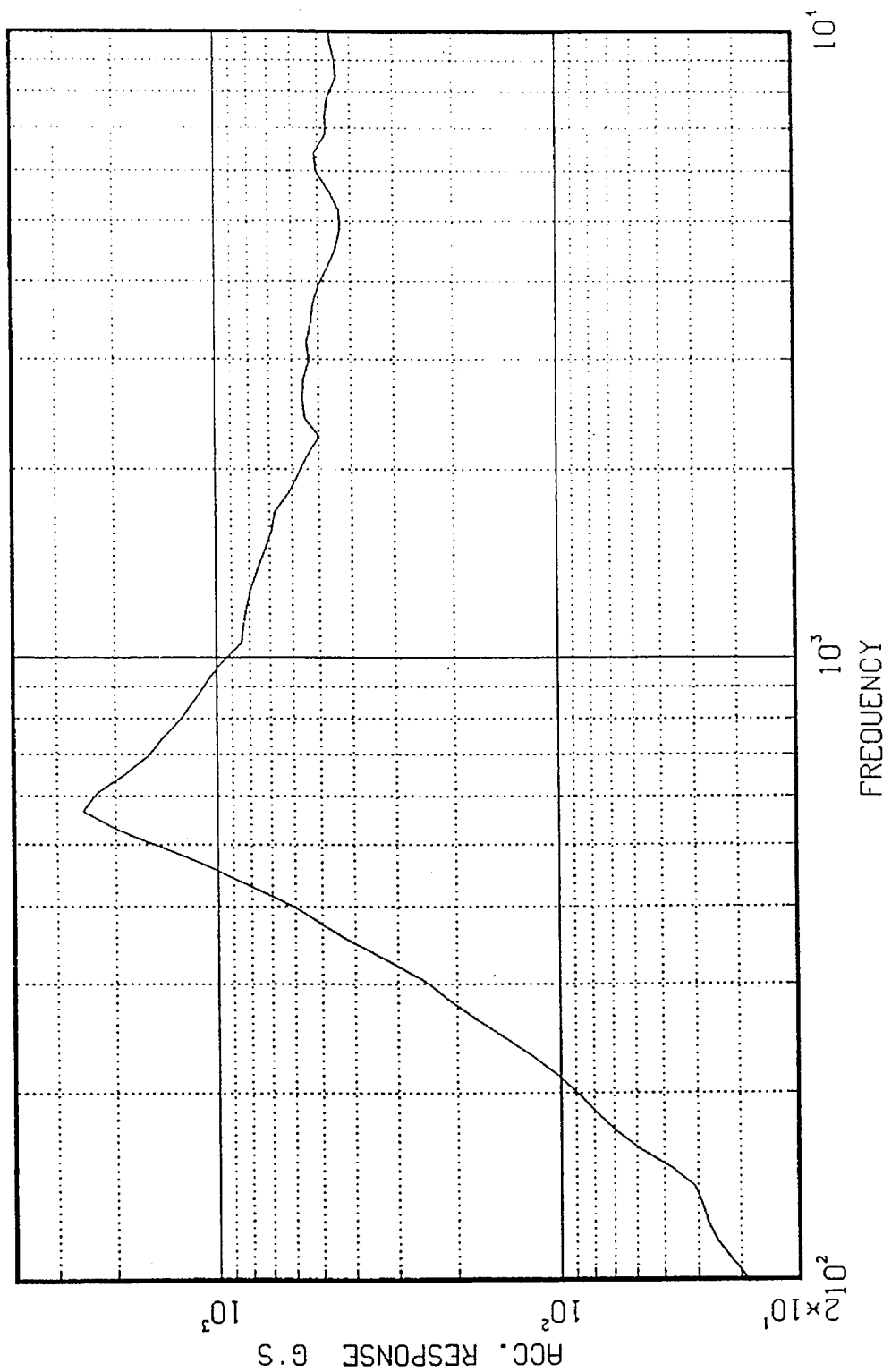
Figure 14A:
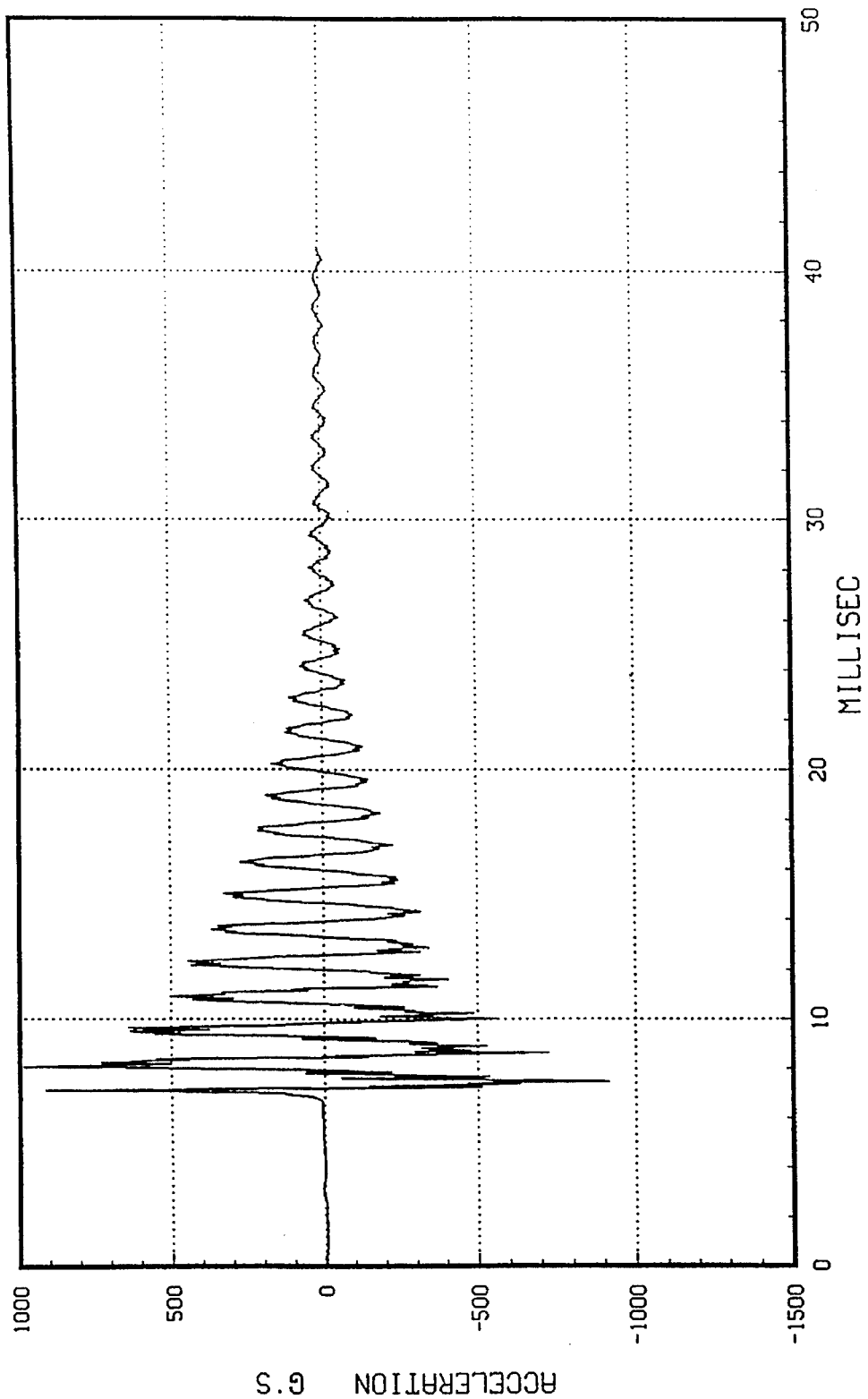
FIGS. 14a and 14b show graphic representations of time history and SRS for a larger apparatus, with a 24" space, with pads.
Figure 14B:
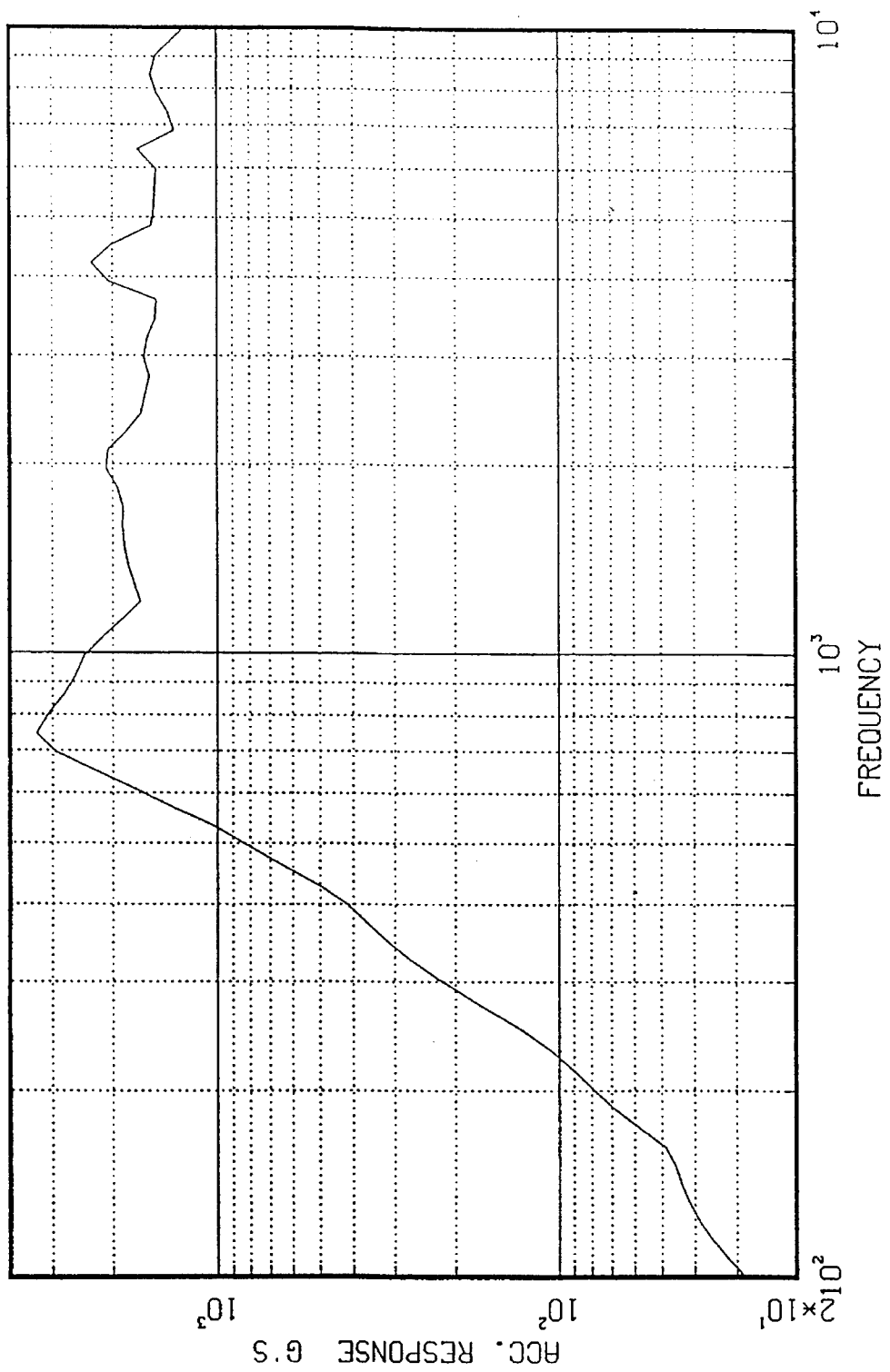
Figure 15A:
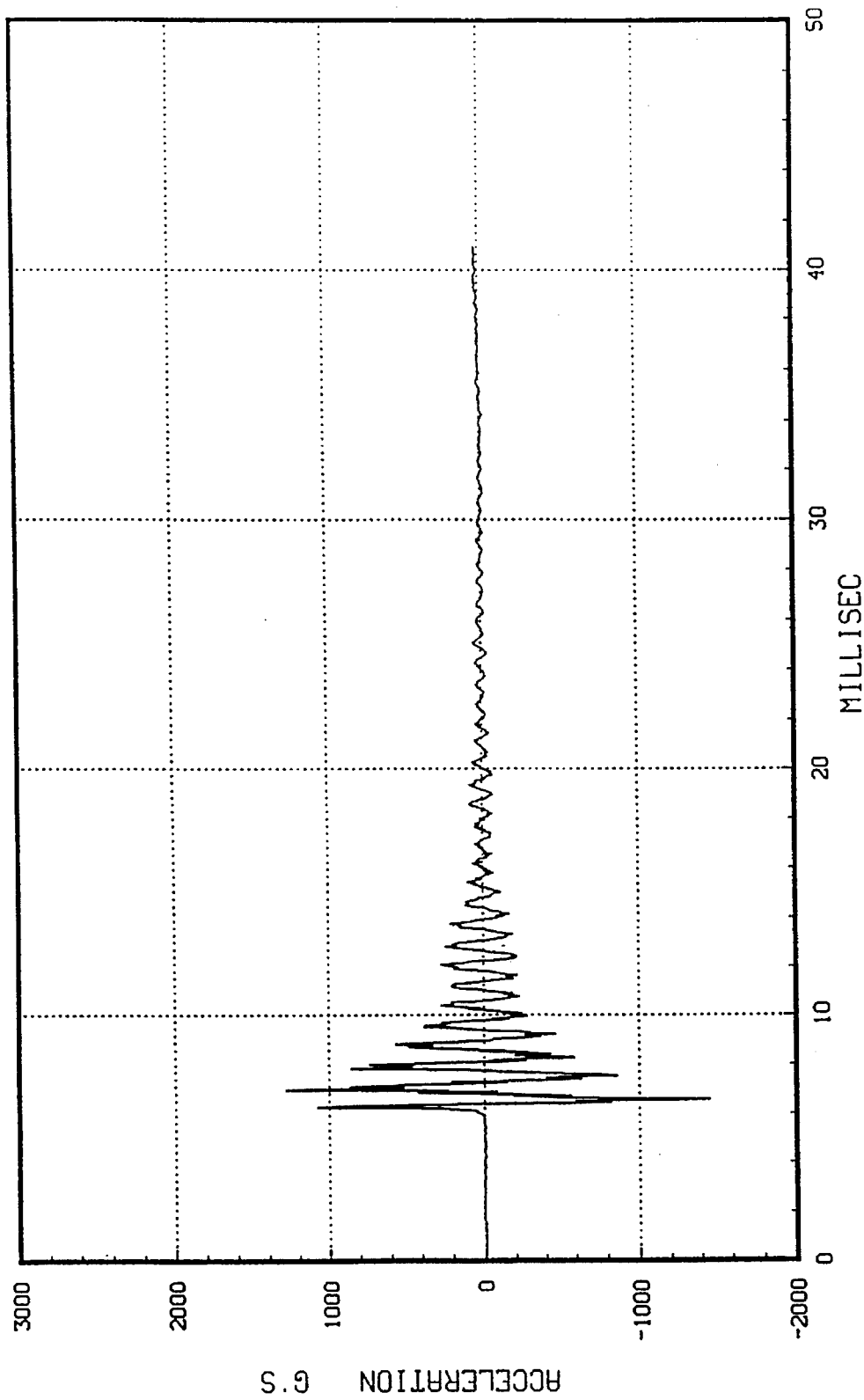
FIGS. 15a and 15b show graphic representations of time history and SRS for a larger apparatus, with a 18" space, with pads.
Figure 15B:
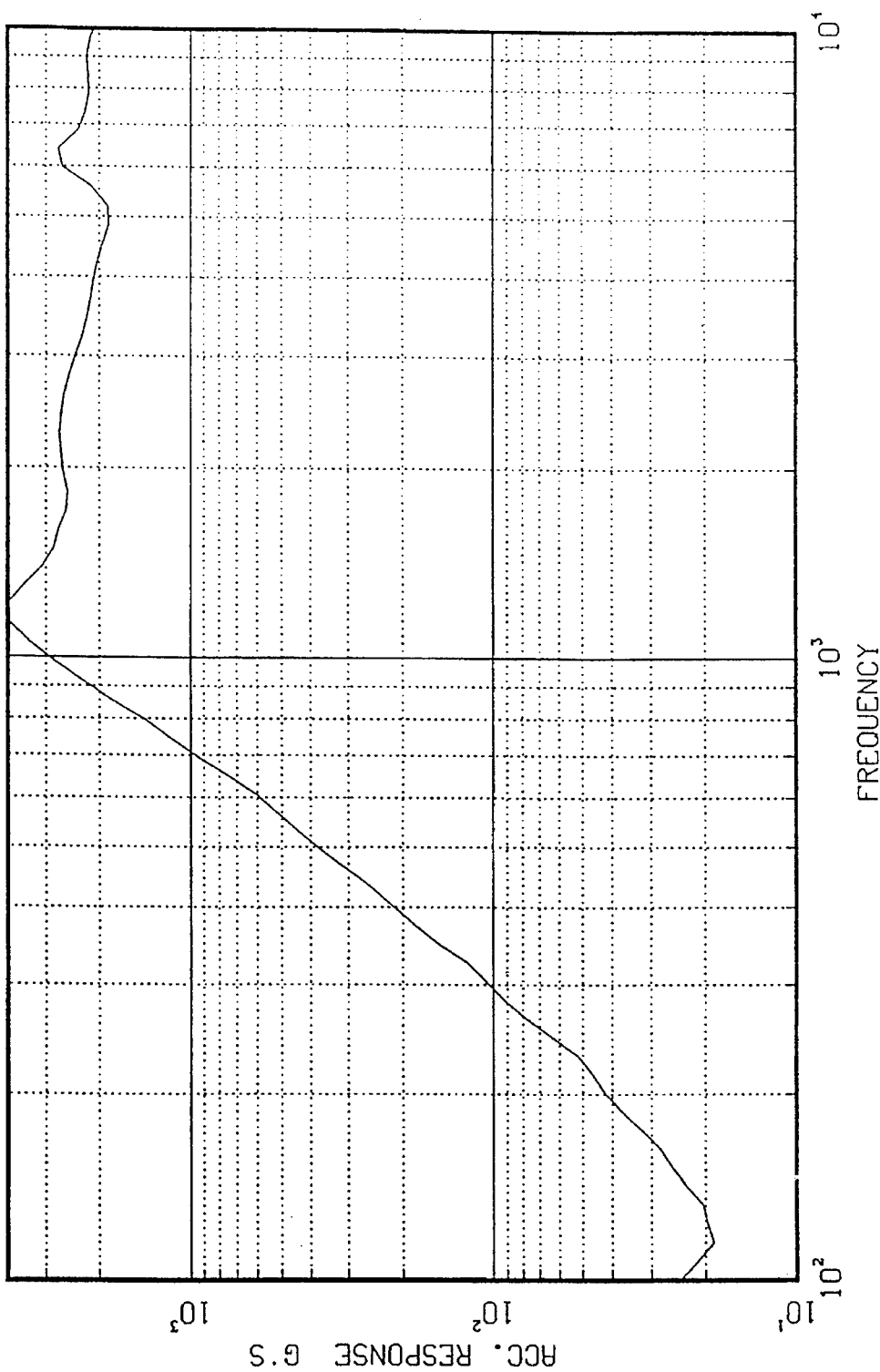

This small scale apparatus was modeled using the ALGOR™ finite dement code. This model was developed so that a predictive tool would be available to aid in the design of a larger tunable resonant fixture. A modal analysis of the model with a 10" spacing between the blocks revealed two dominant bending modes at 890 Hz, and 1070 Hz. These can be compared to the corresponding measured frequencies at 810 Hz, and 900 Hz. The small differences between the experimental results and the analytical model can be explained by the boundary conditions that were assumed for the interfaces between the beam and the blocks. These interfaces were modeled as rigid connections, which resulted in a slightly stiffer structure than the clamped configuration of the actual hardware. FIG. 8 shows the 2 dimensional mesh in its undeformed state, superimposed with an exaggerated mode shape (890 Hz).

The positive results from the small scale testing and analysis justified the design of a larger scale apparatus. The small scale results did not provide enough information to design an apparatus capable of testing 24"×24" components. Instead, a larger tunable resonant fixture with a 10"×10" mounting base capability was designed and built.

Prior to design of the larger apparatus, the following performance criteria were established: 1) The beam resonant frequency must be adjustable from about 500 Hz to about 3000 Hz; 2) The free span of the beam must be greater than 15" for any frequency in this range. Using these criteria, and Equation 1, a 4" thick aluminum beam was selected. Based on Equation 1, a 4" thick aluminum beam with perfectly fixed ends will have a first bending frequency of 630 Hz for a 36" span, and 3600 Hz for a 15" span. These frequency limits were selected higher than the design criteria since the small scale model indicated that the actual resonant frequencies would be lower than those calculated. A total beam length of 72' was selected, which allowed each end of the beam to be clamped with 18" long blocks. Although aluminum was used in this example, other beam materials may also be used including magnesium, steel, titanium, carbon fiber composite or glass fiber composite.

The basic elements of the larger apparatus were then designed and modeled with ALGOR™. Using the modal analysis features of ALGOR™, the tunability of the dominant bending mode of the resonant beam was verified. These analyses also showed several lower amplitude modes at frequencies below the dominant bending mode of the beam. This caused some concern that these lower modes could be excited and interfere with the intended response of the resonant beam. To determine if this might be true, ALGOR™ was used to calculate the transient response of the beam when subjected to a force pulse. This pulse was triangular shaped with a duration of ½ the period of the desired bending mode. The resulting transient response was completely dominated by the desired mode, with no significant influence from the lower modes observed in the modal analysis. These results justified the final design details of the larger apparatus.

FIGS. 9a and 9b are line drawings identifying the major parts of the larger apparatus. FIG. 9a shows a front view and FIG. 9b shows a side view. A simple enlargement of the small scale apparatus would have resulted in two rather large masses that would need some elaborate mechanism to position them at various points along the resonant beam. Instead, referring to FIG. 9, the larger apparatus of the present invention uses a single large mass as a platform (45) to which the resonant beam assembly can be attached using smaller and easily movable clamping plates (50). This platform consists of a 4" thick steel plate which is integrally cast onto the top of a large concrete block (55). Each end of the resonant beam (60) is held between a pair of steel plates which are clamped to the steel and concrete base with a set of 1" diameter threaded rods (65). The ends of the threaded rods are anchored in the base with special nuts (70) that slide in "T" slots machined in the steel plate (similar to a milling machine table). When the upper nuts on the threaded rods are loosened, each pair of clamping plates can be easily repositioned using a hand wheel and ball screw assembly (75). When the nuts are tightened, each clamping assembly approximates a fixed end condition on the resonant beam.

The two sets of clamping plates are normally positioned symmetrically about the center (and impact point) of the beam, but the design allows for independent positioning which will provide the opportunity to investigate non-symmetric configurations. The clamping plates are fitted with pneumatic piston and roller bearing assemblies that, when actuated (with the clamping nuts loose), lift and separate the clamping plates and resonant beam. This roller mechanism allows the clamping plates to be easily moved, and also provides spacing for the insertion of rubber or other damping pads. The resonant beam has a convenient component mounting hole pattern.

A 3" ID air gun barrel (80) is housed in a cylindrical space in the center of the concrete mass. The air gun breech, main valve, and reservoir are within the space (85) under the center of the concrete mass. Other valving and controls (not shown in the Figure) are contained in an enclosure on the back side of the concrete mass. The air gun operates on compressed air or nitrogen, and has a Maximum Allowable Working Pressure (MAWP) of 300 psi. The gun is loaded through the breech which allows the resonant plate assembly to remain in place for this operation. The projectile is a 3" diameter flat nosed aluminum or steel cylinder up to 12" long. The projectile is fired vertically upward to impact the center of the beam, which is then excited into resonance. Alignment of the air gun barrel is not required since it is built into the apparatus design. The gun design is such that the projectile only partially exits the barrel upon impact, and thus rebounds back to the bottom of the barrel where it is in position for the next test. The self-contained nature of the projectile represents a safety improvement over some of the previous pyroshock simulation methods. For safety reasons, the air gun firing mechanism is operated remotely from outside the room containing the apparatus. The impact duration can be easily adjusted by using various thicknesses of felt pads at the point of impact. The weight of the projectile will also affect the impact duration. The amplitude of the beam's resonant response can be adjusted with the impact speed (i.e. air gun firing pressure).

Tests were conducted for six different configurations using the larger apparatus. The results of those tests are summarized in the table below and are illustrated graphically in the Figures noted in the table:

TABLE 1

| Distance between clamps (in.) | Neoprene damping pads | Measured resonant frequency (Hz) | Resonant frequency (Hz) from Eq. 1 | Time history and SRS FIG. No. |
| --- | --- | --- | --- | --- |
| 30 | no | 630 | 900 | 10a and 10b |
| 24 | no | 1000 | 1400 | 11a and 11b |
| 18 | no | 1400 | 2500 | 12a and 12b |
| 30 | yes | 570 | 900 | 13a and 13b |
| 24 | yes | 750 | 1400 | 14a and 14b |
| 18 | yes | 1200 | 2500 | 15a and 15b |

These data show that the resonant frequency is indeed tunable with the apparatus of the present invention. The measured resonant frequencies, are 30% to 50% lower than the frequencies predicted for a perfectly fixed-fixed beam of the same length. This trend was expected based on the small scale results, however, the difference was expected to be smaller. The SRS (FIGS. 10–15) plots show that actual data approximate the desired general shape for pyroshock simulation, and the knee frequency shifts are as predicted with each change in the beam length. The addition of neoprene pads appeared to do more to lower the resonance frequency than it did to increase the damping. Fortunately, the larger scale apparatus in general is more damped than the small scale apparatus. A four-pound aluminum projectile fired at 100 psi was used for all of these tests. The thickness of felt programming pads was adjusted for each configuration so that the input pulse duration was appropriate for the resonant frequency being excited. This thickness was 1¼" for the 30" spacing, and ¾" for the 24" and 18" spacing.

Figure 16:
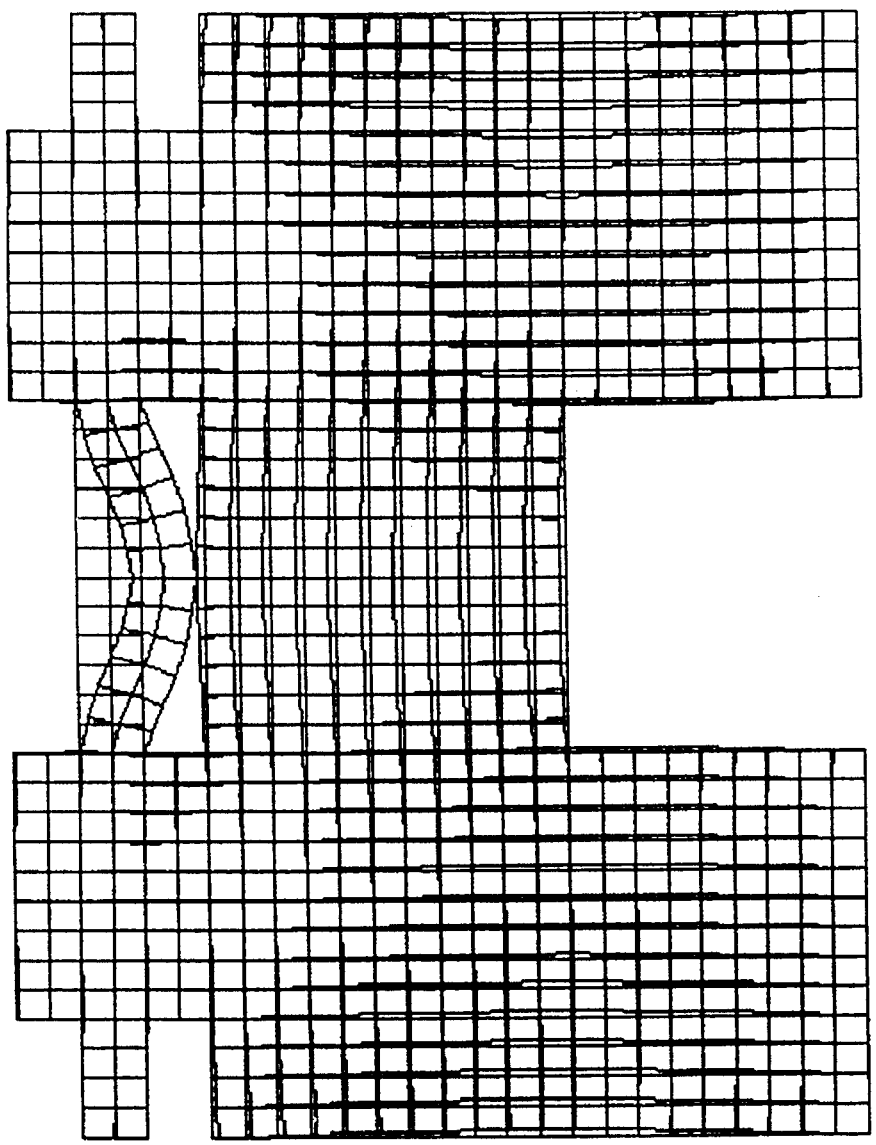
FIG. 16 shows a graphic representation of mode shape of the dominant bending mode of a larger apparatus.
Figure 17A:
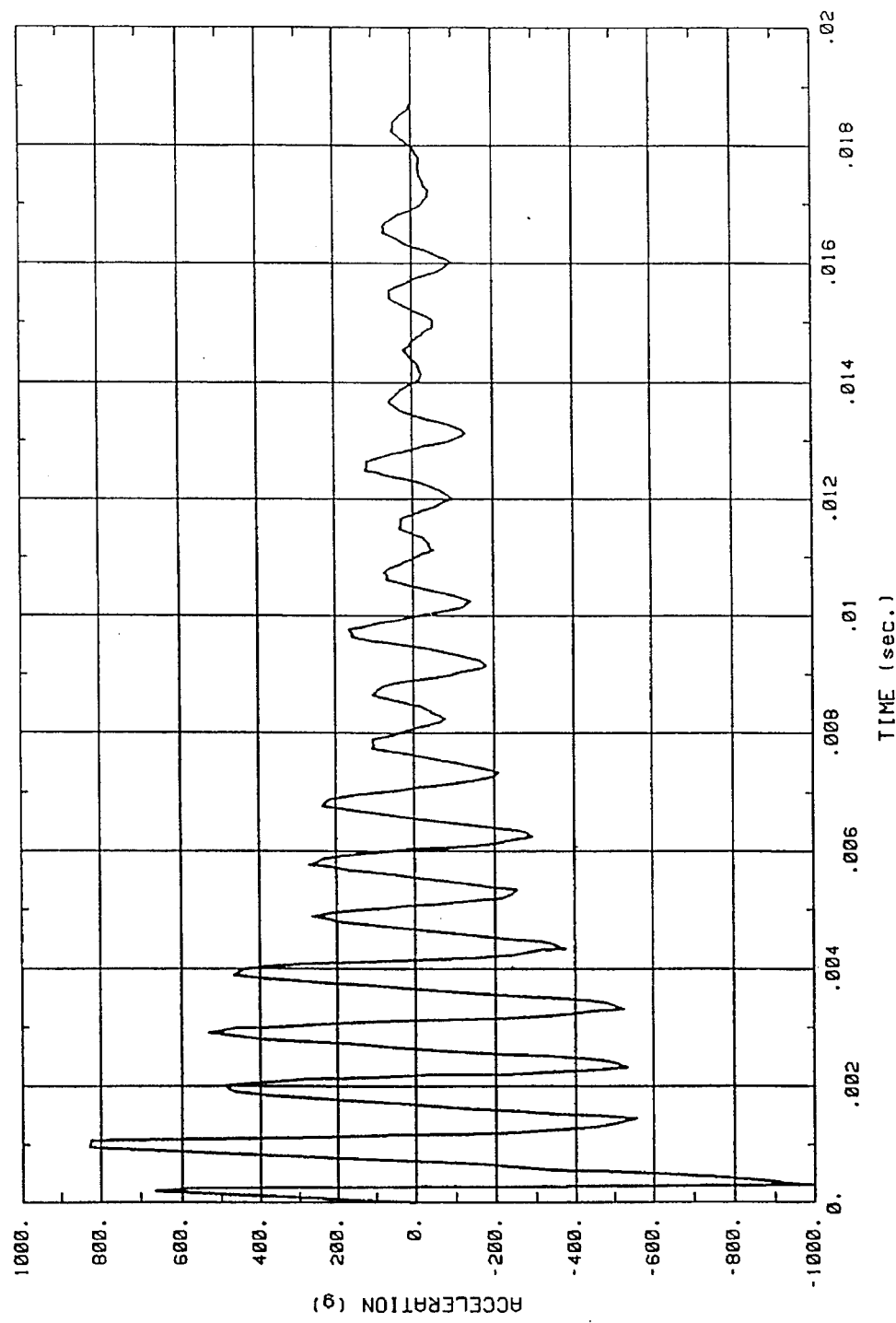
FIGS. 17a and 17b shows a graphic representation of time history and SRS from transient analysis of a larger apparatus, 24" space.
Figure 17B:
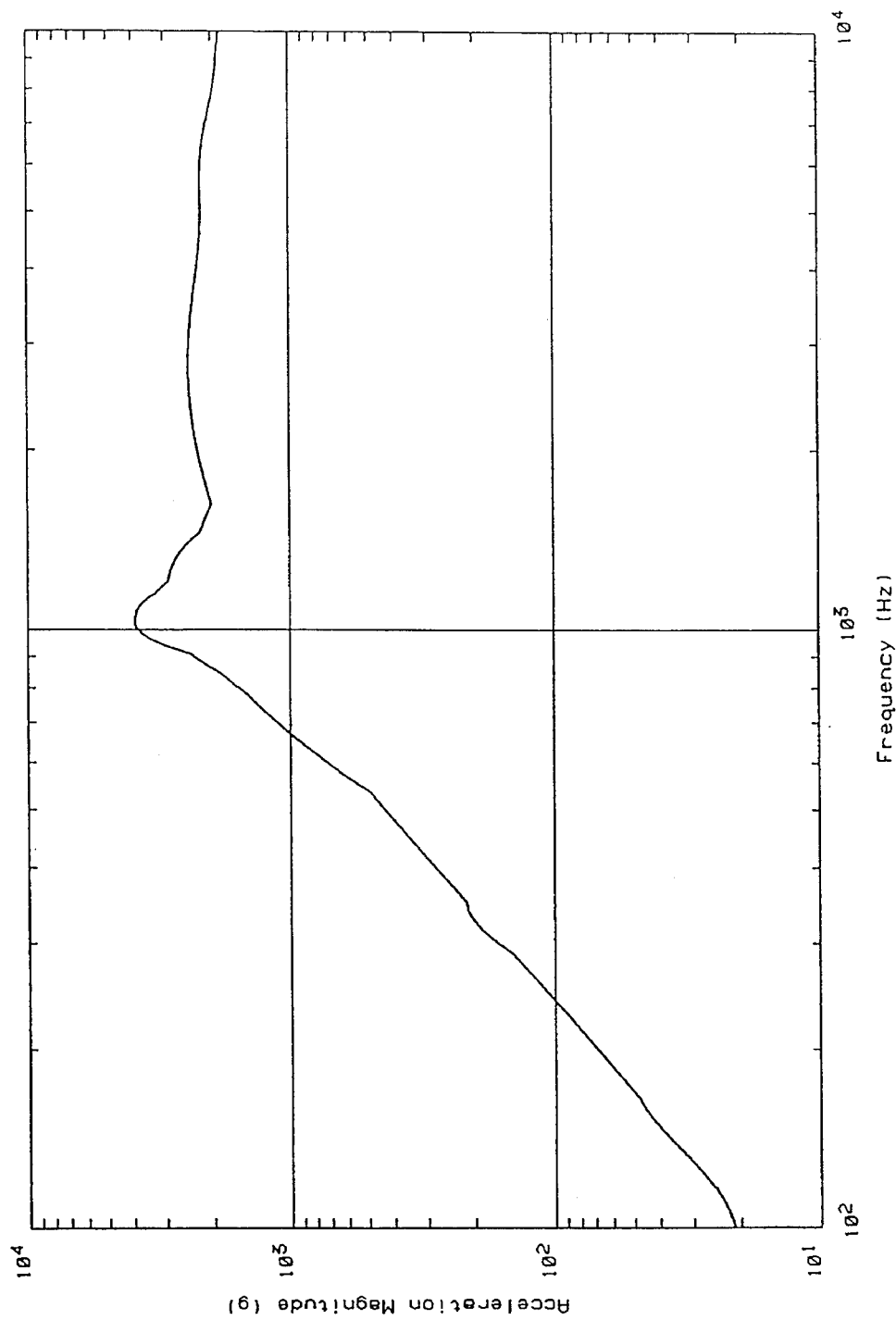

The larger apparatus was also modeled with the ALGOR™ code for the 24" damp spacing. The modal analysis yielded a dominant mode at 1146 Hz (compared to 1000 Hz measured). The exaggerated mode shape is shown in FIG. 16. A transient analysis was also conducted using a triangular force pulse with a 0.5 msec duration. The resulting time history, and SRS are shown in FIGS. 17a and 17b. Similarities are evident in the analytical and experimental SRS plots (FIGS. 11a and 11b and FIGS. 17a and 17b). These results show that the ALGOR™ model can be used as a design tool for extending this test method to a size capable of testing 24"×24" satellite components.

Figure 18A:
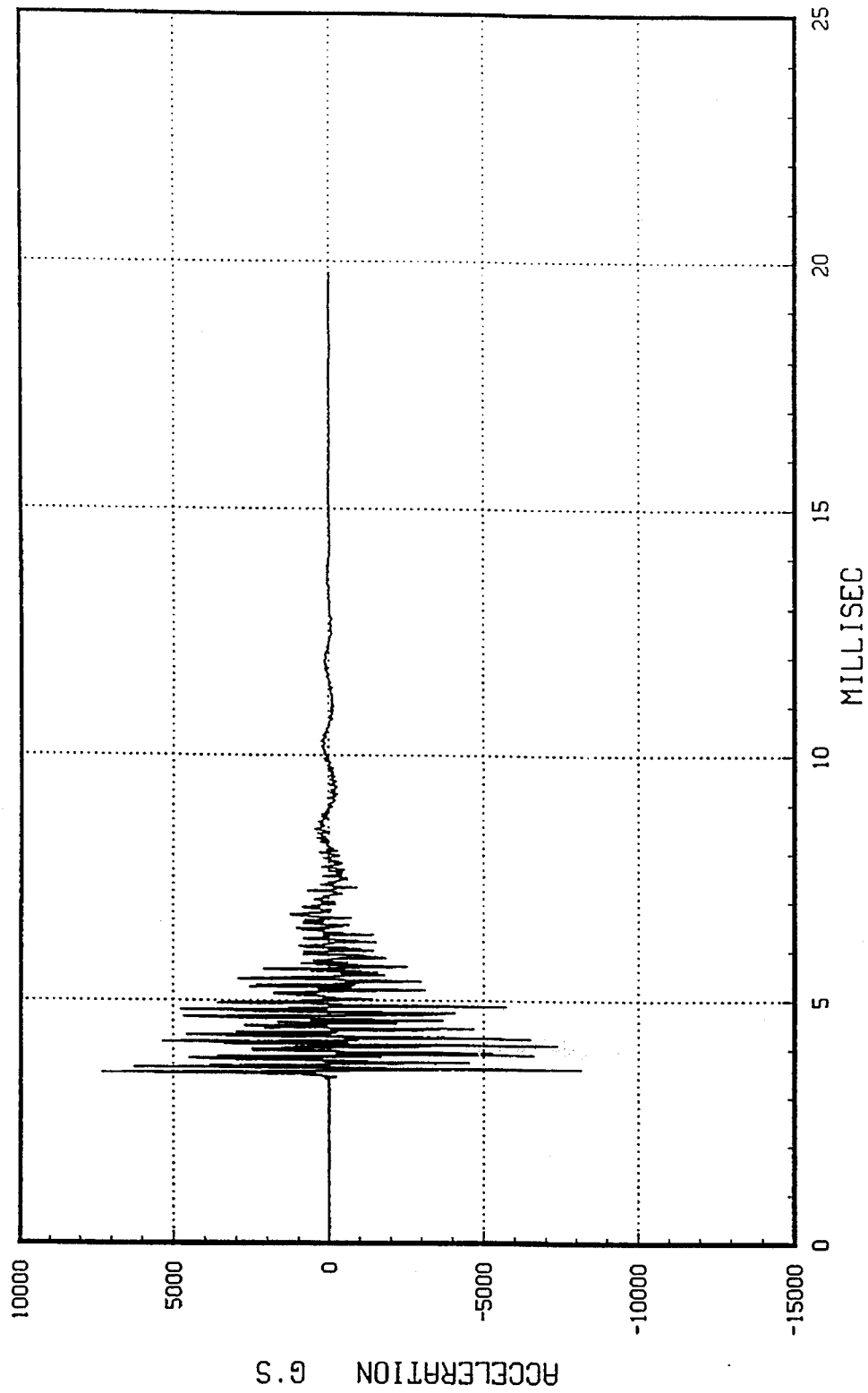
FIGS. 18a and 18b show graphic representations of excitation of higher mode (6 Khz) for larger apparatus, 30" space.
Figure 18B:
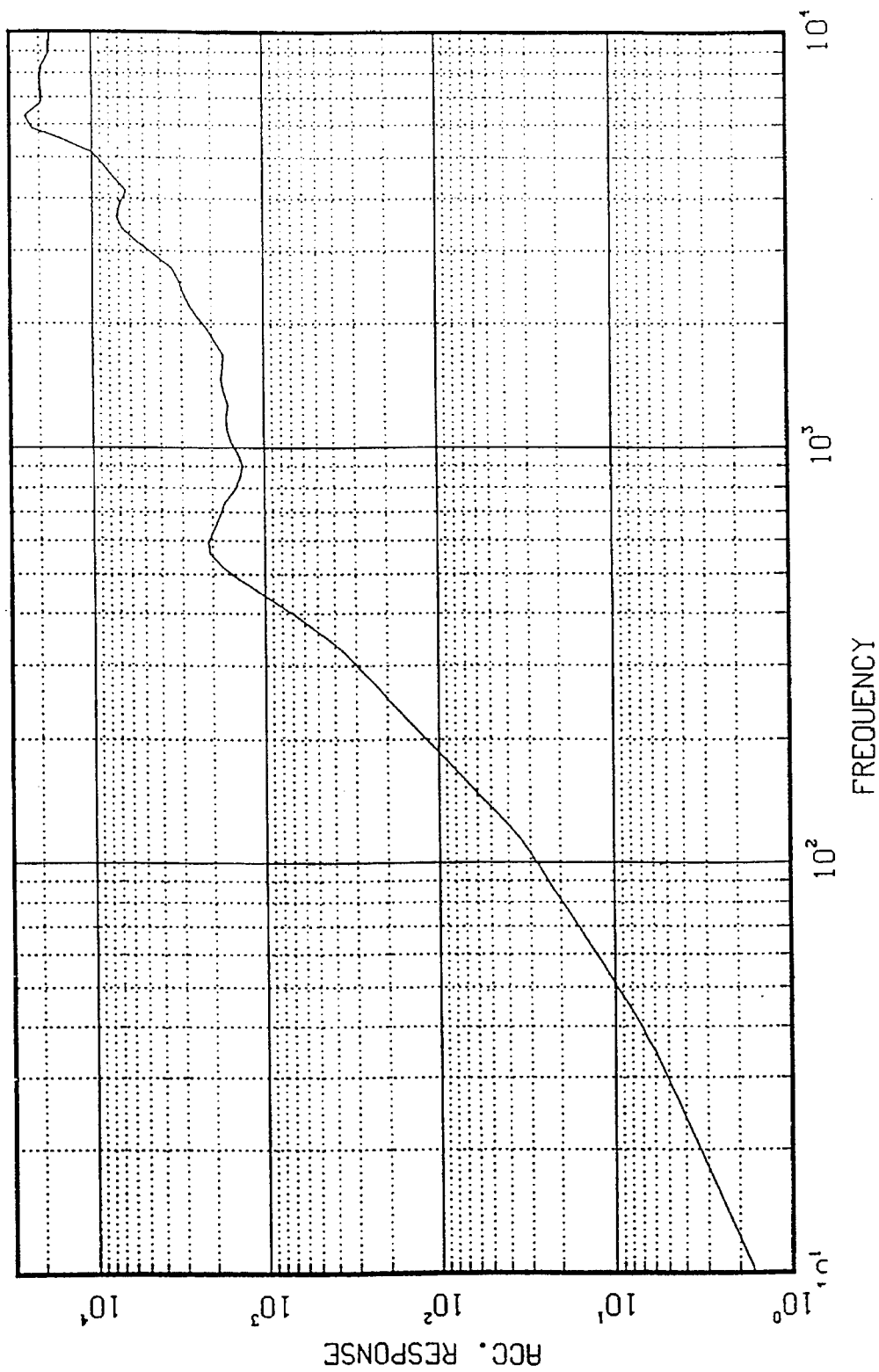

Some additional experiments were conducted to examine the possibility of selectively exciting higher modes of the resonant beam. If this could be done successfully, then the upper frequency limit could be increased without fabricating a thicker (i.e. stiffer) beam. FIGS. 18a and 18b show the results of one of these experiments where the 30" configuration was struck with a much shorter duration pulse, which excited a 6 KHz mode. The dominant response was at 6 KHz, but the first bending mode (630 Hz) was not completely suppressed. This resulted in a SRS with two peaks. With more study, the selective control of higher modes could result in the capability to provide a wide variety of SRS shapes for pyroshock simulation.

Based on data generated using the small scale and larger scale units, the tunable resonant fixture concept and the ability to analytically model the dynamic response of the structure have been demonstrated. A full size apparatus, capable of testing a component with a 24"×24" base, is possible using the principles set forth herein.

I claim:

1. An apparatus for simulating pyrotechnic shock comprising:
   a beam having two ends and a center;
   a first clamping means securing said beam in the region between one end and the center, and a second clamping means securing said beam in the region between the other end and the center, so that a portion of said beam between said first and second clamping means is suspended freely and capable of resonating;
   an impact means capable of striking said beam at a point of impact and exciting a resonance simulating pyrotechnic shock in said beam within said portion or said beam which is suspended freely and capable of resonating;
   an adjustment means enabling said first and second clamping means to be moved along said beam within said regions so that proximity of said first and second clamping means to said point of impact may altered and the length of said portion of said beam which is suspended freely and capable of resonating may be changed; and
   an attachment means capable of securing to said beam a component to be tested.

2. The apparatus of claim 1 wherein said beam comprises material selected form the group consisting of aluminum, titanium, magnesium, steel, carbon fiber composites and glass fiber composites.

3. The apparatus of claim 1 wherein said first and second clamping means each comprise an upper mass and a lower mass.

4. The apparatus of claim 1 wherein said length of portion of said beam which is suspended freely and capable of resonating is selected such that resonance within such portion will exhibit, upon impact, a desired shock response spectrum with respect to the frequency at which the knee frequency occurs.

5. The apparatus of claim 1 wherein said impact means comprises a projectile fired by an air gun and impacting said beam at a point of impact in the region of the center of said beam.

6. The apparatus of claim 5 wherein said attachment means is located on said beam, in the region of the center of said beam, opposite the point of impact of such projectile.

7. The apparatus of claim 1 further comprising at least one damping means affixed to said beam in the region of said point of impact.

8. The apparatus of claim 7 wherein said at least one damping means comprises material selected from the group consisting of felt, paper, plastic, cardboard, neoprene and substance exhibiting characteristics of putty.

9. The apparatus of claim 1 wherein said first and second clamping means comprise a single massive platform to which said beam may be attached with movable first and second clamping plates.

10. The apparatus of claim 9 wherein said single massive platform is integrally cast onto a concrete block.

11. The apparatus of claim 10 further comprising a wheel and ball screw assembly capable of repositioning said first and second clamping plates.

12. The apparatus of claim 11 wherein said adjustment means comprises a pair of pneumatic piston and roller bearing assemblies capable of permitting engagement and disengagement of said first and second clamping plates from said beam.

13. The apparatus of claim 10 further comprising an air gun having a barrel including a bottom positioned vertically in said concrete block with said barrel of said air gun positioned beneath said beam in the region of the center of said beam.

14. The apparatus of claim 13 further comprising a means by which a projectile fired by said air gun partially exits said barrel, impacts said beam, and rebounds back to the bottom of said barrel.

15. A method for simulating pyrotechnic shock comprising the steps of:
   clamping a beam having two ends and a center with a first clamping means securing said beam in the region between one end and the center, and a second clamping means securing said beam in the region between the other end and the center, said first and second clamping means being adjustable and having the capability of being moved along said beam so that their proximity to a point of impact located therebetween on said beam may be altered, whereby said first and second clamping means are positioned so that the portion of said beam between said first and second clamping means is suspended freely and capable of resonating, and the length of said portion is selected to suit specific test requirements for shock response spectrum;
   attaching a component to be tested to said beam with an attachment means;

striking said beam with an impact means at a point of impact, thereby exciting a resonance simulating pyrotechnic shock in said beam within said portion of said beam which is suspended freely and capable of resonating.

16. The method of claim 15 wherein said beam comprises aluminum.

17. The method of claim 15 wherein said first and second clamping means each comprise an upper mass and a lower mass.

18. The method of claim 15 wherein said length of portion of said beam which is suspended freely and capable of resonating is selected such that resonance within such portion will exhibit, upon impact, a desired shock response spectrum with respect to the frequency at which the knee frequency occurs.

19. The method of claim 15 wherein said impact means comprises a projectile fired by an air gun and impacting said beam at a point of impact in the region of the center of said beam.

20. The method of claim 19 wherein said attachment means is located on said beam, in the region of the center of said beam, opposite the point of impact of such projectile.

21. The method of claim 15 further comprising the step of affixing at least one damping means to said beam in the region of said point of impact.

22. The method of claim 21 wherein said at least one damping means comprises material selected from the group consisting of felt, paper, plastic, cardboard, neoprene and substance exhibiting characteristics of putty.

23. The method of claim 15 wherein said first and second clamping means comprise a single massive platform to which said beam may be attached with movable first and second clamping plates.

24. The method of claim 23 wherein said single massive platform is integrally cast onto a concrete block.

25. The method of claim 24 further comprising the step of repositioning said first and second clamping plates using a wheel and ball screw assembly.

26. The method of claim 25 wherein said first and second clamping means are made adjustable by use of an adjustment means comprising a pair of pneumatic piston and roller beating assemblies capable of permitting engagement and disengagement of said first and second clamping plates from said beam.

27. The method of claim 24 further comprising the step of positioning an air gun having a barrel including a bottom vertically in said concrete block with said barrel of said air gun positioned beneath said beam in the region of the center of said beam.

28. The method of claim 27 further comprising the step of firing a projectile with said air gun such that said projectile partially exits said barrel, impacts said beam, and rebounds back to the bottom of said barrel.

* * * * *